(12) United States Patent
Walker et al.

(10) Patent No.: US 11,104,703 B2
(45) Date of Patent: Aug. 31, 2021

(54) BINDING COMPOUND AND USES THEREOF

(71) Applicant: The Queen's University of Belfast, Belfast (GB)

(72) Inventors: Brian Walker, Newcastle Down (GB); Lorraine Martin, Belfast Antrim (GB); Timothy Ferguson, Enniskillen Fermanagh (GB)

(73) Assignee: The Queen's University of Belfast, Belfast (GB)

( * ) Notice: Subject to any disclaimer, the term of this patent is extended or adjusted under 35 U.S.C. 154(b) by 0 days.

(21) Appl. No.: 16/344,122

(22) PCT Filed: Oct. 24, 2017

(86) PCT No.: PCT/GB2017/053205
§ 371 (c)(1),
(2) Date: Apr. 23, 2019

(87) PCT Pub. No.: WO2018/078351
PCT Pub. Date: May 3, 2018

(65) Prior Publication Data
US 2020/0010505 A1    Jan. 9, 2020

(30) Foreign Application Priority Data
Oct. 24, 2016  (GB) ..................................... 1617935

(51) Int. Cl.
| | | |
|---|---|---|
| *C07K 7/02* | (2006.01) | |
| *A61K 47/54* | (2017.01) | |
| *A61P 11/00* | (2006.01) | |
| *C07K 5/02* | (2006.01) | |
| *A61K 38/00* | (2006.01) | |
| *C12Q 1/37* | (2006.01) | |
| *G01N 33/573* | (2006.01) | |

(52) U.S. Cl.
CPC .............. *C07K 7/02* (2013.01); *A61K 47/557* (2017.08); *A61P 11/00* (2018.01); *C07K 5/02* (2013.01); *C12Q 1/37* (2013.01); *G01N 33/573* (2013.01); *A61K 38/00* (2013.01); *G01N 2333/96433* (2013.01); *G01N 2800/382* (2013.01)

(58) Field of Classification Search
None
See application file for complete search history.

(56) References Cited

U.S. PATENT DOCUMENTS

| | | |
|---|---|---|
| 5,550,139 A | 8/1996 | Groutas |
| 2002/0156018 A1 | 10/2002 | Thompson et al. |

FOREIGN PATENT DOCUMENTS

| | | | |
|---|---|---|---|
| EP | 2 470 672 A1 | 7/2012 | |
| WO | 99/29311 A1 | 6/1999 | |
| WO | 20110024006 A1 | 3/2011 | |
| WO | 20160118910 A1 | 7/2016 | |

OTHER PUBLICATIONS

CAS RN 409109-73-5. (Year: 2002).*
CAS RN 121676-60-6. (Year: 1989).*
Gilmore, et al., (2006), "Synthesis, kinetic evaluation, and utilization of a biotinylated dipeptide proline diphenyl phosphonate for the disclosure of dipeptidyl peptidase IV-like serine proteases", Biochemical and Biophysical Research Communications, vol. 347, pp. 373-379.
Pan, et al., (2006), "Development of activity-based probes for trypsin-family serine proteases", Bioorganic & Medicinal Chemistry Letter, vol. 16, pp. 2882-2885.
Cravatt, et al., "Activity-Based Protein Profiling: From Enzyme Chemistry to Proteomic Chemistry", Annu. Rev. Biochem., (2008) vol. 77, pp. 373-414.
Kay, et al., "The synthesis, kinetic characterization and application of biotinylated aminoacylchloromethanes for the detection of chymotrypsin and trypsin-like serine proteinases", Biochem. J., (1992) vol. 283, pp. 455-459.
Cullen, et al., "The application of a novel biotinylated affinity label for the detection of a cathepsin B-like precursor produced by breast-tumour cells in culture", Biochem. J., (1992), vol. 283, pp. 461-465.

(Continued)

*Primary Examiner* — Sudhakar Katakam
*Assistant Examiner* — Zachary J Miknis
(74) *Attorney, Agent, or Firm* — McDonnell Boehnen Hulbert & Berghoff LLP

(57) ABSTRACT

Described are compounds for targeting proteases, e.g. serine proteases and their use in the diagnostic methods and methods for treatment of respiratory diseases such as cystic fibrosis. The compounds have the structure [H]—[B]-[A]; wherein [H] is a hydrophilic group, [B] is a subsite recognition group and [A] is a binding group; wherein A has the formula: —C(0)—$CH_2$—$NR^1$—$COOR^2$ and wherein [B] has the structure: (i) —[CO—$CH_2$—$NR^3$]m-, or (ii) -[AA1-AA2]- or (iii) -(AA1-C0-$CH_2NR^3$)— or (iv) —(CO—$CH_2$—$NR^3$-AA1)- or (v) —(C0—$CH_2$—$NR^4$-AA1-AA3)-.

8 Claims, 21 Drawing Sheets

(56) References Cited

OTHER PUBLICATIONS

McGinty, et al., "Characterization of the cysteine proteinases of the common liver fluke Fasciola hepatica using novel, active-site directed affinity labels", Parasitology, (1993), vol. 106, pp. 487-293.

Gilmore, et al., "Synthesis, kinetic evaluation, and utilization of a biotinylated dipeptide proline diphenyl phosphonate for the disclosure of dipeptidyl peptidase IV-like serine proteases", Biochemical and Biophysical Research Communications, (2006), vol. 347, pp. 373-379.

Gilmore, et al., "Expedited Solid-Phase Synthesis of Fluorescently Labeled and Biotinylated Aminoalkane Diphenyl Phosphonate Affinity Probes for Chymotrypsin- and Elastase-Like Serine Proteases", Bioconjugate Chem., (2009), vol. 20, pp. 2098-2105.

Walker, et al., "The irreversible inhibition of urokinase, kidney-cell plasminogen activator, plasmin and 1-trypsin by 1-(N-6-amino-n-hexyl)carbamoylimidazole", Biochem. J., (1984), vol. 221, pp. 277-280.

Niphakis, et al., "Evaluation of NHS Carbamates as a Potent and Selective Class of Endocannabinoid Hydrolase Inhibitors", ACS Chem. Neurosci., (2013), vol. 4, pp. 1322-1332.

Tran, et al., "Solid-phase Submonomer Synthesis of Peptoid Polymers and their Self-Assembly into Highly-Ordered Nanosheets", Journal of Visualized Experiments, (2011), vol. 57, pp. 1-7.

Reihill, et al., "Inhibition of Protease-Epithelial Sodium Channel Signaling Improves Mucociliary Function in Cystic Fibrosis Airways", American Journal of Respiratory and Critical Care Medicine, (2016), vol. 194, No. (6), pp. 701-710.

\* cited by examiner

Figure 10A QUB-TL1
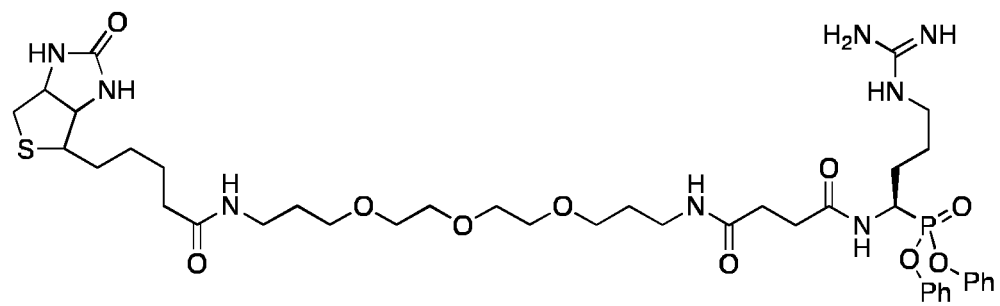
Figure 10B. Effect of serine protease inhibitors on mucociliary clearance.
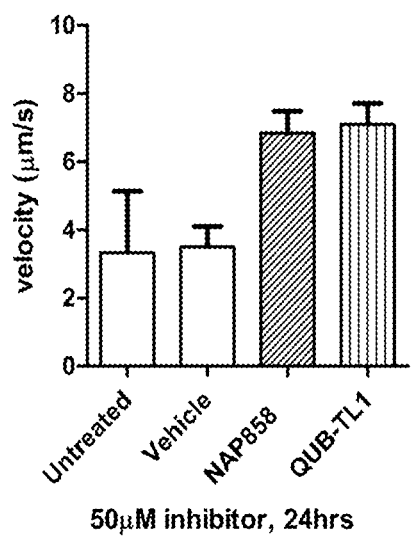

BINDING COMPOUND AND USES THEREOF

CROSS REFERENCE TO RELATED APPLICATIONS

This application is a US national phase of International Application No. PCT/GB2017/053205, filed on Oct. 24, 2017, which claims benefit from GB Patent Application No. 1617935.0, filed on Oct. 24, 2016, the entire contents of each of which are incorporated herein by reference.

FIELD OF THE INVENTION

The present invention relates to compounds for targeting proteases, e.g. serine proteases. Furthermore, the present invention relates to the use of such compounds in the detection and/or inhibition of proteases, their use in diagnostic methods and methods and compounds for treatment of respiratory diseases, in particular the treatment of chronic inflammatory lung disease such as cystic fibrosis (CF).

BACKGROUND OF THE INVENTION

Serine proteases are one of the most widely studied classes of enzymes: this is largely due to their well-characterised, widespread and diverse roles in a host of physiological and pathological processes. Many disorders are caused by a dysfunction in the normal exquisite regulation of the activity of these proteolytic enzymes, resulting in abnormal tissue destruction and/or aberrant processing of other proteins and peptides.

Respiratory disease underlies the majority of patient morbidity and mortality in cystic fibrosis and is characterised by persistent, chronic bacterial infection and inflammation of the airways that, ultimately, leads to airway obstruction, bronchiectasis and death[1]. Hyperactivation of the epithelial sodium channel (ENaC) is a key feature of CF airway epithelial cells contributing to dehydration of the airway surface liquid layer (ASL); regarded as an initiating event in CF pulmonary pathogenesis[2-5].

Regulated endoproteolysis of ENaC subunits ($\alpha$ and $\gamma$), catalysed by a group of serine proteases termed channel activating proteases (CAPs), represents a key regulatory mechanism for increased channel conductance which otherwise remains low due to Na$^+$ self-inhibition[6, 7]. Full activation of ENaC occurs in a step-wise manner with initial activation elicited by the pro-protein convertase furin augmented by the subsequent action of prostasin (CAP1)[8]. It is now evident that CF airways exhibit an imbalance between CAPs and their natural inhibitors, with elevated levels of prostasin and furin reported in CF airway epithelial cell cultures compared with non-CF controls[9-11]. siRNA-mediated knockdown of prostasin reduces ENaC currents by ~70%[12] and this effect is corroborated when camostat mesylate, an inhibitor of prostasin (CAP1) and matriptase (CAPS)[13], is delivered to the nasal epithelium of CF patients[14]. The specific furin inhibitor decanoyl-RVKR-cmk (furin I) decreases basal ENaC currents and augments the inhibitory action of aprotinin (which targets trypsin-like proteinases including prostasin) when added to human CF airway epithelial cells[15].

In addition to modulation of ENaC, trypsin- and furin-like proteinases activate a variety of substrates and signalling mechanisms highly relevant in CF airways. Furin processes surface receptors such as pro-TGFβ1[11, 16, 17], a plethora of extracellular matrix proteins encompassing several matrix metalloproteinases[18, 19], a variety of viral and bacterial proteins including influenza hemagglutin (HA)[20, 21] and *Pseudomonas aeruginosa* exotoxin A (PE)[22-24]. In addition trypsin-like proteases such as human airway trypsin (HAT) have been demonstrated to play a role in the enhancement of mucin gene expression and mucus hypersecretion, inflammation and fibrosis in human airway epithelial cells[25-28].

Protease-Activated Receptors (PARs) are G-protein-coupled, seven transmembrane domain receptors which can be activated by serine proteases by proteolytic cleavage of the N-terminal sequence. The unmasking of a new amino terminus serves as a tethered ligand which binds to conserved regions in the body of the receptor, resulting in the initiation of signal transduction. There are at least 4 in the grouping, however PAR-2 is of particular interest in airways diseases as it is expressed in epithelial and smooth muscle cells as well as fibroblasts. In inflammation mast cells, macrophages and neutrophils also have increased levels of PAR-2 (Cocks and Moffatt, 2001). It is selectively activated by trypsin and trypsin-like (TL) enzymes such as mast cell tryptase (MCT) and human airway tryptase (HAT) (Cocks and Moffatt, 2001), and has a pro-inflammatory action (Dery et al, 1998). PAR-2 is associated with Toll-like receptor-4 (TLR4) and the NF-κB activation pathways which together influence inflammatory processes such as an increased production of cytokines. For example, trypsin has been shown to stimulate the expression of IL-8 by airways cells via activation of PAR-2 coupled to an induction of NF-κB-mediated transcription (Larsen et al, 2008).

PAR-2 activation and its relationship to inflammation in the airways has been most studied in allergic asthma, where the inhibition of PAR-2 was found to significantly inhibit airway hyperresponsiveness (Asaduzzaman et al, 2015). Molecules that inhibit PAR-2 signalling may therefore be considered a therapeutic option in allergic asthma.

In cystic fibrosis (CF) airways excessive levels of serine TL proteases activate the epithelial sodium channel (ENaC) resulting in airways dehydration, a key initiating event for CF lung disease. The present inventors have shown that presence of these TL proteases at clinically relevant levels in the lung may also play a role in PAR-2 activation with relevance across a number of airways diseases including asthma, CF and COPD. In this study TL proteolytic activity was found to relate to clinical outcome in CF. TL protease activity, measured in adult CF sputum, inversely correlated with lung function (FEV1). Individuals with high TL protease activity also demonstrated reduced survival with a significant mortality hazard (HR 1.03, 95% CI 1.01-1.05; p=0.009) (multivariate Cox regression analysis; adjusted for age and BMI). These initial findings were further supported by a validation cohort. This study highlights the potential of TL protease activity as a novel non-invasive biomarker and/or therapeutic target which may impact clinical outcomes in CF, and potentially other chronic airways diseases such as COPD.

Active site-directed, small molecule-based covalent probes have been used to detect various classes of proteases in biological systems[33] and many of the first examples of these activity probes were developed in the inventors' laboratory[34-39]. WO2011024006 describes a number of diagnostic probes for use in the detection and measurement of proteases for use in the detection and measurement of proteases.

SUMMARY OF THE INVENTION

The inventors have identified a class of ligands which can be used to efficiently detect proteases, for example serine proteases. Advantageously, compounds of the invention may be readily produced using solid phase synthesis methods.

According to a first aspect of the invention there is provided a compound which has the structural formula:

[H]—[B]-[A];

wherein [H] is a hydrophilic group, [B] is a subsite recognition group and [A] is a binding group;
wherein A has the formula:

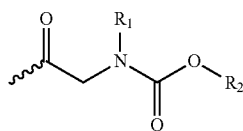

wherein $R_1$ is H, optionally substituted alkyl, optionally substituted heteroalkyl, optionally substituted aryl, or optionally substituted heteroaryl, and
$R_2$ is cycloalkyl, heterocycloalkyl, aryl or heteroaryl, wherein said cycloalkyl, heterocycloalkyl, aryl or heteroaryl moiety is optionally substituted
wherein [B] has the structure:
(i) —[CO—$CH_2$—$NR^3$]$_m$—, or
(ii) -[AA1-AA2]- or
(iii) -(AA1-CO—$CH_2NR^3$)— or
(iv) —(CO—$CH_2$—$NR^3$-AA1)- or
(v) —(CO—$CH_2$—$NR^4$-AA1-AA3)-;
wherein $R^3$ is H or alkyl; m is 1-2; $R^4$ is H, alkyl or a basic group; AA1, AA2 and AA3 are amino acid residues which, when linked to another amino acid; are linked through a reverse amide bond. These amino acids can be of the (L) or (D) configuration. In examples (iii) and (iv) the amino acid and N-alkyl glycine (where $R^3$ is alkyl), or glycine (where $R^3$ is H), residues are linked through a reverse amide bond.

AA1 and AA2 may be any natural amino acid, a (D) isomer of a natural amino acid or ornithine. AA3 may be (i) any natural amino acid, (ii) a (D) isomer of a natural amino acid or (iii) an unnatural amino acid other than a (D) isomer of a natural amino acid.

The new class of ligands may be used to inhibit proteases, such as epithelial sodium channel activating enzymes. The identification of such inhibitors enables the use of the inhibitors in the treatment of a number of conditions, in particular chronic inflammatory lung diseases such as cystic fibrosis.

Accordingly, in a second aspect of the invention, there is provided the compound of the first aspect of the invention for use in medicine.

A third aspect of the invention provides compound of the first aspect of the invention for use in the treatment of inflammatory airway disease.

According to a fourth aspect of the invention, there is provided a method of treating an inflammatory airway disease, said method comprising administration of a compound of the invention to a subject in need thereof.

A fifth aspect of the invention provides a compound of the first aspect of the invention for use in the treatment of renal disease.

According to a sixth aspect of the invention, there is provided a method of treating renal disease, said method comprising administration of a compound of the invention to a subject in need thereof.

In a seventh aspect of the invention, there is provided a pharmaceutical composition comprising a compound of the first aspect of the invention.

In an eighth aspect, the invention provides a method of inhibiting one or more channel activating proteases, said method comprising the administration of a compound of the first aspect of the invention.

In one embodiment, the channel activating protease is selected from the group consisting of human airway trypsin (HAT), matriptase and prostatin.

A ninth aspect provides a method of inhibiting activation of the epithelial sodium channel (ENaC), said method comprising the administration of a compound of the first aspect of the invention.

A tenth aspect provides a method of inhibiting activation of protease-activated receptor (PAR-2), said method comprising the administration of a compound of the first aspect of the invention.

The compounds of the invention may also be used in methods to detect proteases.

Accordingly, in an eleventh aspect, the present invention provides a method for the detection and/or inhibition of one or more proteases, comprising the steps of:
mixing a biological sample with a compound of the first aspect of the invention, allowing the compound to stably bind a target protease in the sample to form a detectable complex and
detecting the detectable complex.

A twelfth aspect provides a method of detecting a pathological condition in a subject comprising the steps of:
providing a sample from the subject,
incubating the sample with a compound of the first aspect of the invention for binding a
protease in order to form a detectable complex, and
determining the amount of protease in the sample through comparison of the amount of the detectable complex present with a standard, and comparing the amount of protease in the sample with a normal level of protease in such a sample, wherein an elevated level of the protease compared to a normal level is indicative of a pathological condition.

A thirteenth aspect of the invention provides an assay system, for example a kit, for the detection of a protease, wherein said assay system comprises a compound of the first aspect of the invention.

Preferred and alternative features of each aspect of the invention are as for each of the other aspects mutatis mutandis unless the context demands otherwise.

DETAILED DESCRIPTION OF THE INVENTION

A compound of and for use in the present invention has the structural formula:

[H]—[B]-[A];

wherein[H] is a hydrophilic group, [B] is a subsite recognition group and [A] is a binding group;
wherein A has the formula:

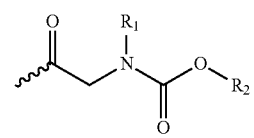

wherein $R_1$ is H, optionally substituted alkyl, optionally substituted heteroalkyl, optionally substituted aryl, or optionally substituted heteroaryl, and R$_2$ is cycloalkyl, heterocycloalkyl, aryl or heteroaryl, wherein said cycloalkyl, heterocycloalkyl, aryl or heteroaryl moiety is optionally substituted;

wherein [B] has the structure:
(i) —[CO—CH$_2$—NR$^3$]$_m$—, or
(ii) -[AA1-AA2]- or
(iii) -(AA1-CO—CH$_2$NR$^3$)— or
(iv) —(CO—CH$_2$—NR$^3$-AA1)- or
(v) —(CO—CH$_2$—NR$^4$-AA1-AA3)-;

wherein R$^3$ is H or alkyl; m is 1-2; R$^4$ is H, alkyl or a basic group; AA1, AA2 and AA3 are amino acid residues which, when linked to another amino acid; are linked through a reverse amide bond. These amino acids can be of the (L) or (D) configuration. In examples (iii) and (iv) the amino acid and N-alkyl glycine (where R$^3$ is alkyl), or glycine (where R$^3$ is H), residues are linked through a reverse amide bond.

AA1 and AA2 may be any natural amino acid, a (D) isomer of a natural amino acid or ornithine. AA3 may be (i) any natural amino acid, (ii) a (D) isomer of a natural amino acid or (iii) an unnatural amino acid other than a (D) isomer of a natural amino acid.

In the context of the present invention, "substituted alkyl" means alkyl substituted by one or more substituents, for example one, two, or three substituents. For example, said substituents may be independently selected from the group consisting of halogen, haloalkyl, haloalkoxy, —OH, —O(C$_1$-C$_6$)alkyl, —CO$_2$H, —CO$_2$(C$_1$-C$_6$)alkyl, —CF$_3$, —NH$_2$, —N(CH$_3$)$_2$, —CONH$_2$, —SO$_2$NH$_2$, —C(=NH)NH$_2$, —CN and —NO$_2$.

"Substituted heteroalkyl" means heteroalkyl substituted by one or more substituents, for example one, two, or three substituents. For example, said substituents may be independently selected from the group consisting of halogen, haloalkyl, haloalkoxy, —OH, —O(C$_1$-C$_6$)alkyl, —CO$_2$H, —CO$_2$(C$_1$-C$_6$)alkyl, —CF$_3$, —N(CH$_3$)$_2$, —CONH$_2$, —SO$_2$NH$_2$, —CN and —NO$_2$.

"Substituted cycloalkyl" means cycloalkyl substituted by one or more substituents, for example one, two, or three substituents. For example, said substituents may be independently selected from the group consisting of halogen, haloalkyl, haloalkoxy, —OH, —O(C$_1$-C$_6$)alkyl, —CO$_2$H, —CO$_2$(C$_1$-C$_6$)alkyl, —CF$_3$, —NH$_2$, —N(CH$_3$)$_2$, —CONH$_2$, —SO$_2$NH$_2$, —C(=NH)NH$_2$, —CN and —NO$_2$.

"Substituted heterocycloalkyl" means heterocycloalkyl substituted by one or more substituents, for example one, two, or three substituents. For example, said substituents may be independently selected from the group consisting of halogen, haloalkyl, haloalkoxy, —OH, —O(C$_1$-C$_6$)alkyl, —CO$_2$H, —CO$_2$(C$_1$-C$_6$)alkyl, —CF$_3$, —NH$_2$, —N(CH$_3$)$_2$, —CONH$_2$, —SO$_2$NH$_2$, —C(=NH)NH$_2$, —CN and —NO$_2$.

An "optionally substituted aryl" means an aryl group substituted with one or more, for example, one, two, three, four, of five groups. In one embodiment, said substituents may be independently selected from the group consisting of halogen, haloalkyl, haloalkoxy, —OH, —O(C$_1$-C$_6$)alkyl, —CO$_2$H, —CO$_2$(C$_1$-C$_6$)alkyl, —CF$_3$, —NH$_2$, —N(CH$_3$)$_2$, —CONH$_2$, —SO$_2$NH$_2$, —C(=NH)NH$_2$, —CN, —NO$_2$, (C$_1$-C$_6$)alkyl, (C$_1$-C$_6$)alkenyl, (C$_1$-C$_6$) alkynyl, optionally substituted cycloalkyl, optionally substituted heterocycloalkyl, and optionally substituted heteroaryl.

An "optionally substituted heteroaryl" means a heteroaryl group substituted with one or more, for example, one, two, three, four, of five groups. In one embodiment, said substituents may be independently selected from the group consisting of halogen, haloalkyl, haloalkoxy, —OH, —O(C$_1$-C$_6$)alkyl, —CO$_2$H, —CO$_2$(C$_1$-C$_6$)alkyl, —CF$_3$, —NH$_2$, —N(CH$_3$)$_2$, —CONH$_2$, —SO$_2$NH$_2$, —C(=NH)NH$_2$, —CN, —NO$_2$, (C$_1$-C$_6$)alkyl, (C$_1$-C$_6$)alkenyl, (C$_1$-C$_6$) alkynyl, optionally substituted cycloalkyl, optionally substituted heterocycloalkyl, and optionally substituted aryl.

A "natural amino acid" is one of the twenty essential amino acids.

An "unnatural amino acid" is an amino acid which is not one of the twenty essential L-amino acids. Unnatural amino acids may include D-amino acids. Other unnatural amino acids may include α-ethyl glycine, αα-dimethyl glycine, N-methyl glycine (sarcosine), α-phenyl glycine, ornithine or β-alanine.

Binding Group [A]

In the compound of and for use in the invention, the binding group [A] comprises a carbamate moiety, for example a succinimidyl carbamate or a pentafluorophenyl carbamate.

The binding group binds serine proteases. Such groups may be able to irreversibly covalently attach to the serine protease, and may discriminate between active and inactive proteases. Without being limited to a particular theory, the inventors believe that the carbamate containing binding group may form an irreversible complex with the active protease, inhibiting protease action. This irreversible action could be of importance in its therapeutic application, since, for example, once the protease is inactivated one does not need to maintain a high concentration of inhibitor. Therefore reduced doses are likely to be effective. In contrast, with a reversible inhibitor, a higher concentration of inhibitor will be required to maintain binding in favour of the natural substrates.

R$_2$ may be any suitable optionally substituted cycloalkyl, heterocycloalkyl, aryl or heteroaryl group which with the —NR$_1$—C(O)—O— motif of [A] forms a carbamate having serine protease binding ability.

In one embodiment, R$_2$ is an optionally substituted aryl group, for example an optionally substituted phenyl group. For example, the optionally substituted phenyl group may be a mono-, di-, tri-, tetra-, or penta-halo substituted phenyl group, wherein the halo substitutions are independently selected from Cl, Br, and F. In one such embodiment, R$_2$ is pentahalo substituted phenyl, such as pentafluorophenyl. In such an embodiment, the carbamate is a pentafluorophenyl-carbamate.

In another embodiment, R$_2$ is an optionally substituted heteroaryl group. Any suitable heteroaryl group may be used. For example, the heteroaryl group may be succinimidyl, quinoline, benzotriazole or 7-azabenzotriazole group. In one embodiment, the heteroaryl group is a succinimidyl group. In such an embodiment, the carbamate is thus a succinimidyl carbamate.

R$_1$ may be any suitable side chain. For example, in one embodiment, R$_1$ is CH(CH$_3$)$_2$. In another embodiment, R$_1$ is benzyl.

The inventors have demonstrated that the inclusion of a basic side chain at position R$_1$ provides binding specificity for trypsin-like proteinases.

In one such embodiment, the basic side chain has a pKb of greater than 8.0.

Such a basic side chain may be protonated.

The basic side chain may comprise a guanidino group. In one such embodiment, R$_1$ comprises a guanidino-substituted phenyl group. For example, R$_1$ may be (C$_{0-6}$) alkyl phenyl wherein the phenyl group is substituted in the meta or para position with a guanidino group. In one embodiment, R$_1$ is (C$_{0-6}$) alkyl phenyl wherein the phenyl group is substituted in the para position with a guanidino group.

In another embodiment, $R_1$ is —$(CH_2)_n$—$R^{13}$; wherein $R^{13}$ is a guanidino group and wherein n is 3, or 4. This side chain is thus equivalent to the basic side chain of arginine or homoarginine. For example, in another particular embodiment, $R_1$ is n-guanidino-propyl.

In another embodiment, $R_1$ is —$(CH_2)_t$—$N^+H_3$, where t is 4 or 5 In such an embodiment in which t is 4, this side chain is thus equivalent to the basic side chain of lysine. Thus, in another example, $R_1$ may be n-amino-butyl.

Where the formulae for the side chains have been recited in their non-protonated form, it should be understood that the invention extends to protonated forms and vice versa.

Advantageously, the compound of and for use in the present invention lacks the ability to bind to proteins other than the serine proteases, and accordingly the compound of the present invention provides a pronounced inhibitory activity with respect to the active serine proteases.

The specific subsite recognition group [B] can be connected to the binding group [A] via any suitable chemical bond. Preferably it is connected via a reverse amide bond.

Subsite Recognition Group [B]

In the compounds of and for use in the present invention, the subsite recognition group [B] has the structure (i) [CO—$CH_2$—$NR^3$]$_m$—, or (ii) -[AA1-AA2]-, or (iii) -(AA1-CO—$CH_2$—$NR^3$)—, or (iv) —(CO—$CH_2$—$NR^3$-$AA_2$)- or (v) —(CO—$CH_2$—$NR^4$-AA1-AA3)- as defined above.

In a particular preferred embodiment of the invention, [B] has the structure: —[CO—$CH_2$—$NR^3$]$_m$—.

In one such embodiment, $R^3$ is H. in a particular embodiment m=2.

In a particular preferred embodiment of the invention, the compound is Biotin-PEG-NH-Gly-Gly-N-(iso-propyl)-glycine succinimidyl carbamate. In another particular preferred embodiment of the invention, the compound is Biotin-PEG-NH-Gly-Gly-N-(benzyl)-glycine succinimidyl carbamate. In a further particular preferred embodiment of the invention, the compound is Biotin-PEG-NH-Gly-Gly-N-(n-guanidino-propyl)-glycine succinimidyl carbamate. In an additional preferred embodiment of the invention, the compound is Biotin-PEG-NH-Gly-Gly-N-(n-amino-butyl)-glycine succinimidyl carbamate. In another embodiment of the invention, the compound is HO-Lys(Biotin)-Ahx-Gly-Gly-N-(n-guanidino-propyl)-glycine succinimidyl carbamate (NAP897) or HO-Lys(biotin)-Ahx-Gly-Gly-N-(n-guanidino-propyl)-glycine pentafluorophenyl carbamate (NAP966).

In a further embodiment of the compound of and for use in the invention, the subsite recognition group [B] can be formed from two amino acid residues -[AA1-AA2]- linked by a reverse peptide bond. These can be of (L) or (D) configuration. In such embodiments, any suitable amino acids may be used. In one such embodiment, AA1 is selected from Lys, Arg, Ser, Thr, and Gln and AA2 is selected from Lys and Arg. Such amino acids are believed to comprise structural motifs, which are recognised by furin. In another embodiment AA1 and AA2 are each Gly.

In a further embodiment of the compound of and for use in the invention, the subsite recognition group [B] has the structure -[AA1-CO—$CH_2NR^3$]— which can be formed from an amino acid AA1 and —CO—$CH_2$—$NR^3$— linked through a reverse amide bond. AA1 can be of (L) or (D) configuration. In such embodiments, any suitable amino acid and —CO—$CH_2$—$NR^3$— group may be used. Where $R^3$ is alkyl, the —CO—$CH_2$—$NR_3$-group is an N-alkyl glycine residue. In one such embodiment, AA1 is selected from Lys, Arg, Ser, Thr, and Gln and the N-alkyl glycine residue is selected from N-(n-amino-butyl)-glycine or N-(n-guanidino-propyl)-glycine.

Likewise, in embodiments in which the subsite recognition group comprises the two amino acid residues linked by a reverse peptide bond, hydrogen bonding is believed to be similarly facilitated by virtue of the reverse amide bond. Moreover, the side chains of the amino acids may also form hydrophobic bonds with the protease.

In a further embodiment of the compound of and for use in the invention, the subsite recognition group [B] can be —(CO—$CH_2$—$NR^4$-AA1-AA3)- where $R^4$ is H, alkyl or a basic group; and AA1 and AA3 are amino acid residues linked through a reverse amide bond.

As described above with respect to position $R^1$ of [A], the inventors have demonstrated that the inclusion of a basic side chain provides binding specificity for trypsin-like proteinases. Similarly, the inclusion of a basic group at position $R^4$ of [B] where [B] is —(CO—$CH_2$—$NR^4$-AA1-AA3)- also provides binding specificity for certain trypsin-like proteinases, such as tryptase and furin.

In one such embodiment where $R^4$ is a basic group, the $R^4$ group has a pKb of greater than 8.0. Such a basic group may be protonated.

In one such embodiment, $R^4$ is —$CH_2$—$(CH_2)_n$—$N^+H_3$ or —$CH_2$—$(CH_2)_n$—$NH_2$.

In another such embodiment, $R^4$ comprises a guanidino group. In one such embodiment, $R^4$ comprises a guanidino-substituted phenyl group. For example, $R^4$ may be $(C_{0-6})$ alkyl phenyl wherein the phenyl group is substituted in the para position with a guanidino group. In another embodiment, $R^4$ is —$(CH_2)_n$—$R^{13}$, wherein $R^{13}$ is a guanidino group and wherein n is 3, or 4.

In one such embodiment of the invention, the compound of or for use in the invention is Biotin-PEG-NH—N-(n-guanidino-propyl)-glycine-Gln-Sar-N-(n-guanidino-propyl)-glycine succinimidyl carbamate (NAP1099). In another such embodiment, the compound of or for use in the invention is Biotin-PEG-NH—N-(n-guanidino-propyl)-glycine-N(Val)-N(Lys)-N-(n-guanidino-propyl)-glycine succinimidyl carbamate (NAP1127).

In another aspect of the invention, there is provided a compound which is N-6-(1-acetylene-3-amino-phenyl)-dicarboxy-pentane-Lys-NH-Ahx-Gly-Gly-N-(n-guanidino-propyl)-glycine succinimidyl carbamate (NAP884) (where Ahx=amino hexanoic acid) or Biotinyl-$(PEG)_2$-N(Arg)-Asn-N-(n-amino-butyl)-glycine succinimidyl carbamate (PRX1305).

Hydrophilic Group

In the compound of and for use in the invention, [H] is any suitable hydrophilic group. The hydrophilic group comprises a capping group and/or a hydrophilic spacer group.

Preferably [H] and [B] are linked via a reverse amide bond.

The term "hydrophilic" as used herein refers to a molecule or part of a molecule that is capable of hydrogen bonding, and which is able to dissolve more readily in water or other polar substances than in oil or other hydrophobic solvents. Such hydrophilic molecules typically have strong polar groups that readily interact with water. A "hydrophilic" group, as the term is used herein, has a solubility in water of at least 100 mg/ml at 25° C.

"Capping Group"

The capping group may comprise, for example, biotin, 2,4-dinitrophenyl, or a derivative thereof, a basic heterocycle such as a morpholinic, piperidyl, or agmantine compound, a sugar based molecule such as a glucoronyl group, or a cyclodextrin, one or more oligosaccharides, one or more di-glucosamine groups, hyaluronic acid, dextran, pectin, collagen, fibrinogen, alginate, antibodies or one or more haptens or antigens. Suitable haptens or antigens which could be used include, for example, His-Tag, FLAG-Tag, Texas Red, green fluorescent protein (GFP), glutathione S-transferase (GST) or similar. The presence of such a capping group may have advantages in inhibiting or reducing degradation of the compound by aminopeptidases.

In one embodiment, the capping group comprises a morpholinic carbamate moiety, a piperidyl carbamate moiety, or an agmatine carbamate moiety. For example, such moieties may have the following structures:

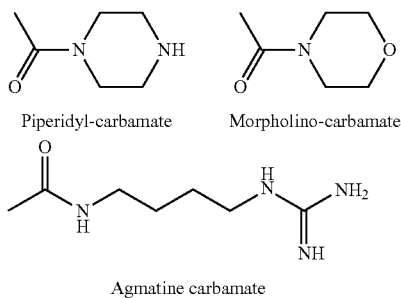

Piperidyl-carbamate       Morpholino-carbamate

Agmatine carbamate

In one particular embodiment, the capping group comprises a biotinyl group, for example

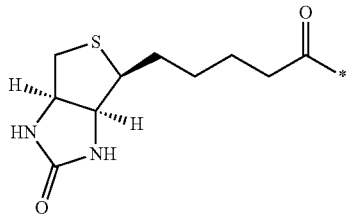 [SMILES: *C(=O)CCCC[C@@H]1SC[C@@H]2NC(=O)N[C@@H]21]

In another embodiment, the capping group comprises a sugar based molecule, such as a glucoronyl group or a cyclodextrin.

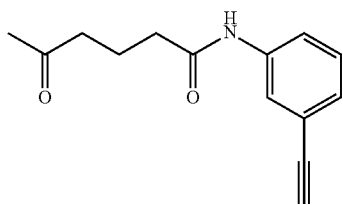 [SMILES: C#Cc1cccc(NC(=O)CCCC(C)=O)c1]

In another embodiment, the capping group comprises a moiety such as (1-acetylene-3-amino-phenyl)-di-carboxy-pentane-, shown above, such as in NAP884, capable of undergoing a click chemistry reaction with a biotinylated azide derivative such as Biotin-Azide (structure shown below).

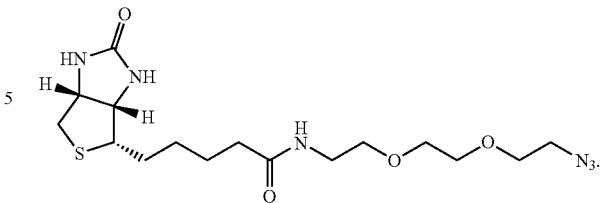

"Spacer Group"

As noted above, the hydrophilic group may comprise, in addition to or as an alternative to the capping group, a hydrophilic spacer group.

Hydrophilic spacer groups which may be used in the invention may include hydrophilic polymers such as polyethyleneglycol, hydroxymethylcellulose, hydroxyethylcellulose polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, polymethyloxazoline, polyethyloxazoline, polyhydroxypropyloxazoline, and polyaspartamide. Other hydrophilic spacer groups which may be used include β-amino acids, γ-amino butyric acid, poly-amino acids, N-alkyl glycines, aliphatic, aromatic or heterocyclic molecules. Capping groups (such as antibodies or biotin) can be attached to hydrophilic spacer molecules thus directing the entire complex to a specific tissue type or cell type. For example, the hydrophilic spacer molecules can also be sugar oligomers with specific attachment points for cell selectins for targeting purposes.

In a particular embodiment, the spacer group may comprise at least one polyethylene glycol (PEG) molecule. In particular embodiments, comprising polyethylene glycol, the polyethylene glycol is in polymeric form. The polyethylene glycol polymer may be in the form of a PEG chain having a molecular weight between about 300 to about 2,000 Daltons, for example between about 500 to about 1,000 Daltons. Such a PEG polymer is believed to provide sufficient hydrophilicity without intertwining of the polymer chain.

Hydrophilic polymers may be employed as homopolymers or copolymers. Where a copolymer is used as the hydrophilic polymer, it may be in the form of an alternating copolymer. A hydrophilic alternating copolymer comprising a first polymer Y and a second polymer Z can have the formula —(—Y—Z)$_n$, where n is two or more. In another embodiment, where a copolymer is used, it may be in the form of a block copolymer i.e. comprising a block of subunits of one subunit type followed by a block of subunits of another subunit type. For example, a block copolymer comprising a first polymer Y and a second polymer Z may have the formula: —(Y)$_{n1}$—(Z—)$_{n2}$, wherein n1 and n2 are independently 2 or more, e.g. —Y—Y—Y—Y—Z—Z—Z.

The polyethylene glycol residues may be employed as part of a hydrophilic copolymer, for example a copolymer of PEG with PLLA, PLDA or PLGA In a particular embodiment of the invention, said spacer moiety has the formula:—NH—(CH$_2$)$_o$—(CH$_2$—CH$_2$—O)$_p$—(CH$_2$)$_q$—NH— or NH—(CH$_2$)$_o$—(CH$_2$—CH$_2$—O)$_p$—(CH$_2$)$_q$—CO—NH—(CH$_2$)$_r$—NH—; wherein o is 0-50, for example 0-10, 10-30, or 30-50; p is 1-100, for example 1-20, 20-50 or 50-100, and q is 0-50, for example 0-10, 10-30, or 30-50, and r is 0-50, for example 0-5, 5-25, or 25-50.

In one such embodiment, o is 0, 1, 2 or 3; p is 1-10, q is 0, 1, 2 or 3, and r is 0, 1, 2 or 3.

For example, in such an embodiment, said spacer moiety may have the formula:

—NH—(CH$_2$)—(CH$_2$—CH$_2$—O)$_2$—(CH$_2$)$_3$—NH—;
NH—(CH$_2$—CH$_2$—O)$_3$—(CH$_2$)$_3$—NH—;
NH—(CH$_2$—CH$_2$—O)$_4$—(CH$_2$)$_3$—NH—;
NH—(CH$_2$—CH$_2$—O)$_2$—CH$_2$—CO—NH—CH$_2$—NH—;
NH—(CH$_2$—CH$_2$—O)$_3$—CH$_2$—CO—NH—(CH$_2$)$_2$—NH—; or
NH—(CH$_2$—CH$_2$—O)$_4$—CH$_2$—CO—NH—(CH$_2$)$_2$—NH—.

In one embodiment of the invention, the hydrophilic group comprises the structure:

R$^5$S(O)$_2$—NH—, R$^5$C(O)—NH—, R$^5$(O)—NH—, R$^5$C(O)O—NH—; R$^5$S(O)$_2$-[spacer]-NH—, R$^5$C(O)-[spacer]-NH—, R$^5$(O)-[spacer]-NH—, or R$^5$C(O)O-[spacer]-NH—; wherein R$^5$ is alkyl, aryl or biotinyl and said [spacer] moiety comprises at least one polyethylene glycol molecule.

Thus, in some embodiments, the hydrophilic polymer may be a PEG polymer capped at one end. In some embodiments, the capping group is alkoxy. For example, a hydrophilic polymer useful in the composition as disclosed may be capped with a methoxy group. In another preferred embodiment the capping group may comprise a biotin moiety.

In one embodiment of the invention, the compound of and for use in the invention is not cell permeable.

In a further embodiment, compounds of and for use in the invention do not inhibit thrombin catalysis of fibrin clot formation.

Production of Compounds of and for Use in the Invention

In one embodiment, the compounds of the invention are formed by solid phase synthesis.

In particular, the invention is believed to make possible the solid phase synthesis of the desired active site-directed compounds, including the 'on-resin' derivatization with, for example, a capping group, e.g. a biotin based capping group, and the incorporation of a spacer group e.g. a pegylated spacer unit. The solution phase incorporation of biotin into peptides is often slow and necessitates the use of excess biotin to drive the reaction to completion. This, in turn, means that extensive purification is needed to obtain the desired product free from contaminating, unbound biotin.

Therapeutic Uses

The present invention may be used in the treatment of diseases associated with overactivity of trypsin-like proteinases.

"Treatment" includes any regime that can benefit a human or non-human animal. The treatment may be in respect of an existing condition or may be prophylactic (preventative treatment). Treatment may thus include curative, alleviation or prophylactic effects.

For example, the present invention may be used in the treatment of inflammatory diseases such as inflammatory airway diseases and inflammatory skin disorders.

Inflammatory airway diseases for which the present invention may find use include cystic fibrosis (Mayer-Hamblett et al., 2007), chronic obstructive pulmonary disease (COPD) (Djekic et al., 2009), non-CF bronchiectasis, emphysema, congenital alpha1-antitrypsin deficiency and acute respiratory distress syndrome (ARDS) (Hayakawa et al., 2010).

In particular embodiments of the invention, the compounds may be used in the treatment of cystic fibrosis. As described above, compounds described herein have been shown to inhibit one or more key ENaC activating enzymes, for example trypsin, HAT, prostasin and matriptase. In one embodiment, the compound of the invention inhibits at least two, for example three, or all four of trypsin, matriptase, prostasin and HAT. In another embodiment, a compound of the invention is capable of inhibiting the protease activity of each of trypsin, matriptase, prostasin and HAT.

The present invention may also be used in other diseases in which trypsin-like proteases and/or furin play a role.

For example, the present invention may find use in the treatment of a number of renal diseases. Accordingly, in a further embodiment of the invention there is provided a method of treating renal disease comprising administration of a compound which has the structural formula: [H]—[B]-[A], as defined above.

For example, the invention may be useful in the treatment of chronic renal disease, renal fibrosis, Liddle's syndrome etc.

Serine trypsin like proteases are associated with a number of skin disorders, the trypsin like proteases being found at the cell surface. Accordingly, in a further embodiment of the invention there is provided a method of treating an inflammatory skin disorder comprising administration of a compound which has the structural formula: [H]—[B]-[A], as defined above. Inflammatory skin disorders which may be treated using the invention include for example atopic eczema, atopic dermatitis, Rocacaea, or psoriasis vulgaris.

The compounds and methods of the present invention may also find use in the treatment of various cancers. For example, blockage of trypsin-like proteases such as matriptase at the cell surface inhibits prostate cancer bone metastasis.

Furthermore, matriptase is highly expressed in breast cancer, ovarian cancer and colorectal cancer. Other cancers from which an overexpression of matriptase has been demonstrated include pancreatic cancer, papillary thyroid cancer, kidney cancer, lung cancer and liver cancer. The trypsin-like serine protease DESC1 is differentially expressed in squamous cell carcinoma of the head and neck.

In one embodiment, the cancer which may be treated using a compound of the invention is selected from the group comprising pancreatic cancer, thyroid cancer, kidney cancer, lung cancer, liver cancer, squamous cell carcinoma of the head and neck, prostate cancer, prostate cancer bone metastasis or soft tissue sarcoma.

Pharmaceutical Compositions

The compounds of and for use in the invention may be administered as a pharmaceutical composition. Pharmaceutical compositions according to the present invention, and for use in accordance with the present invention may comprise, in addition to active ingredients, a pharmaceutically acceptable excipient, a carrier, buffer, stabiliser or other materials well known to those skilled in the art (see, for example, Remington: the Science and Practice of Pharmacy, 21st edition, Gennaro A R, et al, eds., Lippincott Williams & Wilkins, 2005). Such materials may include buffers such as acetate, Tris, phosphate, citrate, and other organic acids; antioxidants; preservatives; proteins, such as serum albumin, gelatin, or immunoglobulins; hydrophilic polymers such as polyvinylpyrrolidone; amino acids such as glycine, glutamine, asparagine, histidine, arginine, or lysine; carbohydrates; chelating agents; tonicifiers; and/or surfactants.

The pharmaceutical compositions may also contain one or more further active compounds selected as necessary for the particular indication being treated, preferably with complementary activities that do not adversely affect the activity of the compound or composition of the invention. For example, for the treatment of conditions such as cystic fibrosis, the compounds described in the present application may be combined with other therapeutic agents such as mucus thinning drugs, bronchodilators, antibiotics, antimicrobial drugs etc.

The active ingredients may be administered via microspheres, microcapsules, liposomes, or other microparticulate delivery systems. For example, active ingredients may be entrapped within microcapsules which may be prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions. For further details, see Remington: the Science and Practice of Pharmacy, 21st edition, Gennaro A R, et al, eds., Lippincott Williams & Wilkins, 2005.

Administration

As described herein, in some embodiments, the methods and uses of the present invention are particularly suitable for the treatment of airway disease. Accordingly, in some embodiments, the compounds for use in the invention may be provided in pharmaceutical compositions adapted for administration via inhalation. Accordingly, a composition of and for use in the invention may be formulated and/or administered to a patient in solid or liquid particulate form such that it may be administered in aerosol form directly via inhalation to the respiratory system. The active compounds may be prepared in solid or liquid particulate forms in particles of a size sufficiently small to be inhaled into the bronchi and alveoli of the lungs. The preparation and delivery of therapeutics by aerosol methods as well known in the art (see for example U.S. Pat. Nos. 5,767,068, 5,508,269, and WO1998 043 650).

The compounds for use in the present invention can thus be provided for inhalation therapy in the form of an inhaler or nebuliser. For inhalation therapy, the therapeutic agents, such as the compounds described herein may be delivered to the respiratory tract as defined solid particles or as a liquid aerosols. In a pharmaceutical aerosol, the pharmaceutical compounds can be provided in a mixture of a fluid carrier and propellant, the aerosol being in the form of a solution, suspension, emulsion, powder or semi-solid preparation. The preparation of aerosols for inhalation therapy is well known in the art. Propellants which may be used in the preparation of the aerosol include propellants such as fluorinated hydrocarbons or compressed gases.

As an alternative to an inhaler, pulmonary delivery of components of and for use in the present invention may be achieved using a nebuliser. Nebulisers generate very fine liquid particles in a gas, for example dispersed as droplets about 5 mm in diameter. The droplets may be carried by air or oxygen from the nebuliser to the respiratory tract of a patient.

Other means by which the compounds of for use in the present invention may be delivered to a patient include mists, intra-oral sprays, metered dose inhalers and dry powder generators, as are conventionally known in the art. For example, see Gonda, J. Pharm. Sci. 940-945 2000.

As described above, the compounds and methods of the present invention find particular use in diseases of, for example, the lung, such as cystic fibrosis. The hydrophilic group of the compounds of and for use in the invention prevents the compounds entering the systemic circulation, thus minimising side effects.

In other embodiments, where it is desired to treat other tissues or organs, targeting of the compounds of the invention may be useful to prevent or minimise side effects on non target tissues and organs. For example, targeting constructs, such as immunoconjugates comprising a compound of the invention, may be used.

An immunoconjugate comprises an "active therapeutic agent" conjugated to e.g. an antibody fragment. Methods of producing immunoconjugates are well known in the art; for example, see U.S. Pat. No. 5,057,313, Shih et al., Int. J. Cancer 41: 832-839 (1988); Shih et al., Int. J. Cancer 46: 1101-1106 (1990), Wong, Chemistry Of Protein Conjugation And Cross-Linking (CRC Press 1991); Upeslacis et al., "Modification of Antibodies by Chemical Methods," in Monoclonal Antibodies: Principles And Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering And Clinical Application, Ritter et al. (eds.), pages 60-84 (Cambridge University Press 1995), and U.S. Pat. Nos. 4,699,784; 4,824,659; 5,525,338; 5,677,427; 5,697,902; 5,716,595; 6,071,490; 6, 187,284; 6,306,393; 6,548,275; 6,653,104; 6,962,702; 7,033,572; 7,147,856; and 7,259,240.

Immunoconjugates may comprise whole antibodies or any suitable antibody fragments. Fragments of antibodies may retain the binding ability of the intact antibody and may be used in place of the intact antibody. Examples of antibody fragments include Fab, Fab', F (ab')2, Fd, dAb, and Fv fragments, scFvs, bispecific scFvs, diabodies, linear antibodies (see US patent 5, 641, 870, Example 2; Zapata etal., Protein Eng 8 (10): 1057-1062 [1995]); single-chain antibody molecules; nanobodies and multispecific antibodies formed from antibody fragments.

The Fab fragment consists of an entire L chain (VL and CL), together with VH and CH1. Fab' fragments differ from Fab fragments by having additional few residues at the carboxy terminus of the CH1 domain including one or more cysteines from the antibody hinge region. The F (ab') 2 fragment comprises two disulfide linked Fab fragments.

Fd fragments consist of the VH and CH1 domains.

Fv fragments consist of the VL and VH domains of a single antibody.

Single-chain Fv fragments are antibody fragments that comprise the VH and VL domains connected by a linker which enables the scFv to form an antigen binding site. (see Pluckthun in The Pharmacology of Monoclonal Antibodies, vol. 113, Rosenburg and Moore eds., Springer-Verlag, New York, pp. 269-315 (1994).

Diabodies are small antibody fragments prepared by constructing scFv fragments (see preceding paragraph) with short linkers (about 5-10 residues) between the VH and VL domains such that inter-chain but not intra-chain pairing of the V domains is achieved, resulting in a multivalent fragment, i.e. a fragment having two antigen-binding sites (see, for example, EP 404 097; WO 93/11161; and Hollinger et al., Proc. Natl. Acad. Sci. USA, 90: 6444-6448 (1993)).

Nanobodies are single-domain antibodies of about 12-15 kDa in size (about 1 10 amino acids in length). Nanobodies can selectively bind to target antigens, like full-size antibodies, and have similar affinities for antigens. However, because of their much smaller size, they may be capable of better penetration into solid tumors. Nanobodies may be produced by immunization of camels, llamas, alpacas or sharks with target antigen, following by isolation of mRNA, cloning into libraries and screening for antigen binding. Nanobody sequences may be humanized by standard techniques (e.g., Jones et al, 1986, Nature 321: 522, Riechmann et al, 1988, Nature 332: 323, Verhoeyen et al, 1988, Science 239: 1534, Carter et al, 1992, Proc. Nat'l Acad. Sci. USA 89: 4285, Sandhu, 1992, Crit. Rev. Biotech. 12: 437, Singer et al, 1993, J. Immun. 150: 2844). Humanization is relatively straight-forward because of the high homology between camelid and human FR sequences.

Nanobodies are also described in, for example, U.S. Pat. Nos. 7,807,162; 7,939,277; 8,188,223; 8,217,140; 8,372,398; 8,557,965; 8,623,361 and 8,629,244.

Targeting constructs need not comprise an antibody or antibody fragment. They may instead comprise a non-antibody targeting molecule conjugated to a compound of the invention. For example, instead of antibodies, the targeting molecule may be an avimer, an aptamer, an affibody, or a fynomer.

Avimers (Silverman et al, 2005, Nat. Biotechnol. 23: 1493-94; Silverman et al, 2006, Nat. Biotechnol. 24:220) are multidomain proteins which have similar affinities and specificities to antibodies for various target molecules. They may comprise multiple independent binding domains. The preparation of and methods of use of avimers are disclosed, for example, in U.S. Patent Application Publication Nos. 20040175756, 20050048512, 20050053973, 20050089932 and 20050221384.

In certain embodiments, the targeting constructs may comprise phage display peptides. Targeting peptides selective for a given target tissue, cell or molecule may be selected and isolated using conventional panning techniques (see, e.g. Pasqualini and Ruoslahti, 1996, Nature 380:364-366; Pasqualini, 1999, The Quart. J. Nucl. Med. 43: 159-162).

In further embodiments, a targeting construct for use in the invention may comprise an aptamer. An aptamer may comprise a conventional RNA or DNA molecule or may comprise modified oligomers. Typically, an aptamer for use in a targeting construct will comprise at least 5, such as at least 10 or 20 nucleotides.

Affibodies (Nord et al, 1995, Protein Eng 8:601-8; Nord et al, 1997, Nat Biotechnol 15:772-77) are small proteins that act as antibody mimetics and were developed by combinatorial engineering on an alpha helical protein scaffold. Affibodies may be produced by randomization of thirteen amino acids involved in the Fc binding activity of the bacterial protein A (Nord et al., 1995; 1997).

Fynomers (available from COVAGEN AG (Zurich, Switzerland) are based on the human Fyn SH3 domain as a scaffold for assembly of binding molecules. Fynomers may be linked together to yield a multispecific binding protein with affinities for two or more different antigen targets. Fynomers are commercially available from COVAGEN AG (Zurich, Switzerland).

Dose

The compounds for use in the invention are preferably administered to an individual in a "therapeutically effective amount", this being sufficient to show benefit to the individual.

As a rough guideline, doses may be given in amounts of 1 ng/kg-500 mg/kg of patient weight, (for example, about 10 ng/kg to about 100 mg/kg, about 50 ng/kg to about 10 mg/kg, about 10 ng/kg to about 1 mg/kg, about 10 ng/kg to about 100 ng/kg, about 10 ng/kg to about 10 µg/kg). Other dosages may be appropriate. The compound of the invention may be administered in a single daily dose or in the form of individual doses, such as from 1 to 4 times, 1 to 3 times, or 1 to 2 times per day. The precise dose will be at the discretion of the physician and will depend upon a variety of factors, including the activity of the particular compound, the age, sex, and general health of the patient, the means and time of administration, and the severity of the condition being treated.

Assays

As described above, compounds of the invention may be used in assays which themselves represent aspects of the present invention. Thus in one aspect, the invention extends to a method for the detection and/or inhibition of a protease in a sample, comprising the steps of:

mixing a sample, particularly a biological sample, with a compound of the first aspect of the invention as hereinbefore and hereinafter described, allowing the compound to stably bind a target protease in the sample to form a detectable complex, and detecting the detectable complex.

Typically the protease is a serine protease. Typically the serine protease may be an elastase-like protease, for example neutrophil elastase (NE) or similar, a trypsin-like protease, for example the majority of KLKs, or a chymotrypsin-like protease, for example PSA, KLK-7 and KLK-9 or similar. According to one embodiment, the serine protease may be a neutrophil-derived protease such as neutrophil elastase, cathepsin G, proteinase-3 or similar. In a particular embodiment, the serine protease is NE.

The sample may be a biological sample which may be derived from a cell, tissue, organ, body fluid, fluid derived from body cavity and/or a potentially pathological site, e.g. a site of potential inflammation, malignancy or the like, a lavage fluid or similar.

Typically the body fluid is saliva, blood, lymph fluid, gingival crevicular fluid, airways fluid, for example induced or expectorated sputum or bronchoalveolar lavage, supernatant from a tissue homogenate or cell preparation, faecal fluid, ascites or wound fluid or the like. Cells or tissue may be appropriately processed to yield a fluid e.g. using a buffer, a cell lysis buffer or the like and maceration, homogenation and/or centrifugation. Lavage fluid may suitably be bronchoalveolar lavage fluid. The lavage fluid may for example be derived from bronchoscopy of CF, COPD, lung cancer, bronchiectasis or other chronic or acute airways disease patient.

The fluid derived from a potentially pathological site may suitably be gingival crevicular fluid from periodontal disease patients. It is particularly preferable to determine neutrophil-derived serine proteases in the crevicular fluid from periodontal disease patients, as these proteases are associated with periodontal disease.

In one embodiment of assays where a fluid and/or tissue is derived from a potentially pathological site, for example a site exhibiting malignancy, the serine protease to be detected may be kallikrein and/or plasminogen activator.

Optionally, the biological sample e.g. sputum may suitably be processed, for example washed with buffer and vortexed, lysed, homogenised, centrifuged, at least partially fractionated, at least partially purified or the like. Blood may be fractionated to yield either plasma or serum.

The amount of compound to be added depends on the type of biological sample and the protease to be detected. Typically, for detection of an active protease 1 to 10 µl of a 10 mM solution of compound is added per ml of an aqueous biological sample; more suitably 5 µl of a 10 mM solution of compound is added per ml of an aqueous biological sample.

The time delay between mixing the sample and the compound and detecting the detectable complex depends upon the amount of sample to be assessed, and the active protease to be detected. Typically the time delay will be 5 minutes to 1 hour, suitably less than 30 min. The method of the present invention thus provides a quick, practical and reliable method of detecting and/or inhibiting target protease/proteases. This enables the routine detection of proteases, for instance in clinics and hospital laboratories.

According to one embodiment of a method of the invention utilising a compound of the invention, the method for the detection comprises the use of an Enzyme Linked Immunosorbent Assay (ELISA). Typically the detectable complex is captured through contact with a substrate comprising a capture group which binds to the detectable complex immobilizing it onto the substrate. Typically the capture group can bind to the reporting group. Suitably in an embodiment the substrate can be coated with a capture group comprising streptavidin, and the reporting group can be biotin. Any suitable substrate may be used such as plate(s), beads, disc(s), particles, array(s) or the like. The complex of the compound of the invention and protease wherein the complex is bound to a substrate may be detected by, for instance, immunodetection using a specific antibody-enzyme conjugate to the protease, for example the active protease.

In certain embodiments, the detecting antibody, e.g. in the case of an elastase assay, would be anti-(species e.g. human) neutrophil elastase and could be either a monoclonal or a polyclonal antibody containing an enzyme conjugate such as horseradish peroxidase (HRP), alkaline phosphatase (AP) or the like. Quantification of the bound, active protease would therefore be through the conversion of a complementary substrate to a readable product e.g. chromogenic substrates such as 3,3',5,5'-tetramethylbenzidine (TMB), 2,2'-Azinobis [3-ethylbenzothiazoline-6-sulfonic acid (ABTS) or o-phenylenediamine dihydrochloride (OPD) for conversion by HRP or in the case of AP, p-Nitrophenyl Phosphate (PNPP); or any suitable chemiluminescent, chemifluorescent or raman substrate for development with HRP.

Alternatively, a specific non-neutralising (i.e. where binding to the protease does not interfere with the exposure of the protease's active site to the compound) antibody-conjugate to the protease may be added to the biological sample before or during mixing with the compound of the present invention. According to one embodiment the antibody and the compound of the present invention are added to the biological sample in a single step. For example, the required reagents may be added simultaneously or a premix comprising the required reagents is added. The simultaneous addition of the required reagents would reduce the overall assay time.

The simultaneous addition of the required reagents is particularly appropriate where the antibody would not interfere with the active site of the protease. The simultaneous addition of the required reagents may also be particularly appropriate where the biological sample is in the form of a crude mix such as a cell lysate, partly purified protein mixture or the like.

The complex of the compound of the invention and a protease may be immobilized as noted above, and detected accordingly. In general, the same methods of detection may be used regardless of whether the antibody is added to the mixture before or after addition of the compound of the present invention. Alternatively, the solid support/substrate may be coated with a specific non-neutralising antibody which may be used to immobilize the protease onto the solid support. The compound may then be added to the assay after an appropriate wash step to irreversibly bind with the antibody-immobilised protease and the complex detected by the addition of an appropriate conjugate. For example, in a case where a reporter group on the compound is biotin, then a streptavidin-HRP conjugate is able to bind to the reporter group and the complex quantified through conversion of a suitable HRP substrate as noted above.

In embodiments, the assay can be carried out at room temperature. Alternatively, the assay can be carried out at suitable elevated temperatures, for example 30° C. to 38° C., e.g. approximately 37° C. It will be appreciated that results can be obtained faster if the reaction temperature is at or close to the optimum reaction temperature, generally 30 to 38° C., for example approximately 37° C.

Preferably, at least one suitable wash step is performed to at least partially purify the protease. Typically the wash step is performed after formation, but before detection of the detectable complex. Any suitable washing solution known to the skilled man may be used, such as a wash buffer, for example a phosphate buffered saline or tris-buffered saline, preferably containing 0.05% (v/v) Tween-20.

Depending on the solid support substrate and the mechanism of capture i.e. either by capture antibody or compound, the method may include the step of blocking of unbound sites on the solid support, typically before the sample is mixed with the compound. This step may be effected through the addition of a suitable peptide, protein or protein mixture, such as bovine serum albumin, ovalbumin, casein, gelatin, skimmed milk or the like.

Preferably, the step of detecting the detectable complex is performed using at least one suitable substrate, preferably an aqueous substrate, capable of conversion to a detectable product, in particular a differently coloured product. According to one embodiment the substrate is 3, 3', 5, 5'-Tetramethylbenzidine (TMB) or p-nitrophenyl phosphate. The substrate can be converted by either horseradish peroxidase or alkaline phosphatase conjugated to either streptavidin or a specific antibody.

Additionally, or alternatively, suitable fluorogenic, luminescent or raman substrates can be used. As will be appreciated, such substrates can increase detection sensitivity down to nano and picogram levels.

The method of the invention has the advantage that it is highly specific, as the specific subsite recognition group of the compound is recognised by a specific recognition sequence of the target protease. Furthermore, the method provides good detection sensitivity as the compound has a high affinity to the target protease.

Where the method of detection is performed on a control sample, preferably at least 90 percent of the protease present is detected. Suitably 95 to 100 percent of the protease present is detected; advantageously approximately 99 percent of the protease present is detected.

According to one embodiment the method may be used to detect more than one protease in a sample through the use of more than one compound of the present invention, where each compound of the present invention added to the sample has a different affinity. Typically more than one protease is detected in a sample. Each compound of the present invention may be added to the sample simultaneously or sequentially.

According to another aspect of the present invention, there is provided a compound of the invention for use in the detection and/or inhibition of proteases, particularly active serine proteases.

According to a further aspect of the present invention, there is provided a method of detecting or monitoring of a pathological condition in a subject comprising the steps of:

providing a sample from the subject,
incubating the sample with a compound of the first aspect of the invention in order to form a detectable complex and
determining the amount of protease in the sample through, analysis of the amount of the detectable complex present, comparing the amount of protease in the sample with a normal level of protease in such a sample,
wherein an elevated level of the protease compared to a normal level is indicative of a pathological condition.

The percentage increase of protease will be dependent on the target protease, as well as on the nature of the pathological condition. Typically the amount of active protease is increased by at least 10-fold compared to the normal level, and can exceed 100-fold depending on the disease and health status of the patient. Typically active proteases are not detected in healthy individuals at such elevated levels. For instance, active proteases are generally not detected in the lungs of healthy individuals.

The normal level of protease may be a range, in which case the amount of protease in the sample is compared to the upper range of the normal range.

For example, an increase of 5-fold or more may be generally indicative of a pathological condition. Typically pathological conditions may be associated with an increase of up to 100-fold or more.

According to one embodiment, the pathological condition is inflammation, including airways diseases such as cystic fibrosis (Mayer-Hamblett et al., 2007), chronic obstructive pulmonary disease (Djekic et al., 2009), bronchiectasis, emphysema, congenital alpha1-antitrypsin deficiency and acute respiratory distress (ARDS) (Hayakawa et al., 2010); atherosclerosis (Henriksen and Sallenave, 2008), pancreatitis (Frossard et al., 2001); acute periodontal disease (Özçaka et al., 2010); solid malignancy (Sato et al., 2006) and haematological malignancy e.g. leukaemias; disseminated intravascular coagulation, sepsis (Hayakawa et al., 2010), aneurysm (Gaetani et al., 1998), or chronic non-healing wound (Trengove et al., 1996), or a bacterial, viral or fungal infection or the like. As discussed herein, it would be advantageous to provide a rapid method of detecting active proteases, as the determination of active proteases can be useful in diagnostic and/or prognostic tests. It may be useful to detect a broad set of active proteases or one or more of a particular protease, for example selected from elastase, chymotrypsin-like or trypsin-like protease; metalloproteinases, such as gelatinases, matrilysin or intestinal collagen; cysteine, for example cathepsin, B, L, S or caspases.

Using the linked reporter group (capping group and spacer)—specific recognition sequence and binding group (capture ligand (warhead)) compounds of the present invention, assay test kits may be used to specifically and selectively detect proteases from test samples.

The assay test kits may utilise ELISA to quantify the level of protease in a sample, lateral flow device such as dipstick technology or protease chip technology.

Assay kits may suitably be used to investigate either diagnostically or prognostically diseases or conditions such as, for example, respiratory diseases (cystic fibrosis, bronchiectasis and COPD), cancer, leukaemia, cardiovascular disease and bacterial infection.

Additionally, the kits may be used in drug discovery to screen libraries of compounds for the identification of specific inhibitors, which could be used for example as anti-protease therapies in a range of pathological disorders. Accordingly, such drug screening assays wherein a test compound and a compound of the present invention are provided to a protease and the inhibition of the binding of the compound of the invention to the protease in relation to the presence of a test compound can be a further aspect of the present invention.

Advantageously, the kit of the present invention measures active proteases, and not proteases which have already been inactivated through neutralisation with an endogenous inhibitor and are therefore no longer capable of causing tissue damage, propagating inflammation or activating other biochemical entities. For example, NE is inactivated in a 1:1 stoichiometric manner by its native inhibitor alpha$_1$-antitrypsin. Once bound it is subjected to degradation and no longer clinically relevant. Measurement of this protein would therefore not be useful for either diagnosis or prognosis. Standard antibody-only ELISAs detect total protease protein which in the case of NE would encompass both active free NE and inactive complexed NE/AAT.

According to a further aspect of the present invention, there is provided an assay system or kit for detection of a protease, comprising a compound as hereinbefore and/or hereinafter described.

In one embodiment, the assay system may be in the form of an ELISA assay, lateral flow device including dipstick, chip, or the like.

In a preferred embodiment, the method for the detection is an ELISA (Enzyme Linked Immunosorbent Assay). The ELISA can include selective capture of a complex formed from the protease and the compound of the present invention using a substrate comprising a capture group such as streptavidin. Suitably the substrate can be in the form of a streptavidin coated plate(s), bead(s) or the like. Following capture of the complex on the substrate the complex can be detected, for example by immunodetection using a specific antibody to the protease or the like. Alternatively, immunocapture using a specific antibody to the protease can also be used to selectively target and/or isolate the protease in a crude mix, such as a cell lysate, partly purified protein mixture or the like, prior to the addition of the compound for subsequent detection. In this case subsequent detection can be performed by the formation of a biotin-streptavidin-peroxidase conjugate formed from the complex of the compound and the capture protease. This may be performed as a single step reaction. For example, use of an antibody which does not interfere with the active site of the protease may allow the simultaneous provision of antibody and the compound of the present invention to a sample. For example, in a particular assay system format the required reagents can be added simultaneously or a premix comprising the required reagents is added, thus reducing the overall assay time.

The ELISA format is advantageous, since it provides a quantitative format, which is labour and time friendly, typically 3.5 hr and normally no more than 4 hrs.

In particular, the ELISA format is advantageous for assaying active NE, which can be captured by a compound being specific for NE. A subsequently applied specific antibody-conjugate provides additional signal amplification, thereby providing much greater sensitivity.

Incubation with the antibody will typically take 5 min to 2 hours, for example approximately 1 hour. This short term incubation is particularly advantageous, as results can be quickly obtained.

As will be appreciated, a lateral flow device or dipstick assay format is also advantageous as it is robust, convenient and easy to use. Furthermore, it may easily be incorporated into the routine assessment of patients either at point of care or for personal monitoring as an at-home test kit. It will be appreciated that the lateral flow device/dipstick assay format is particularly useful in the clinic for a qualitative and possibly semi-quantitative result which could aid patient monitoring and provide an early marker which could inform clinical decisions regarding treatment, including prophylactic treatments.

The kit may further comprise at least one suitable detection agent, which is capable of detecting, e.g. binding to, a reporter group of the compound as hereinbefore and hereinafter described.

Preferably, the kit comprises a suitable support, e.g. a solid matrix support. The matrix support may be a membrane such as nitrocellulose, a resin, such as N-MCA-N$^1$-FMOC-ethylene-diamine MPB-AM resin (typically sold under the trade name NovaTag™) or the like. Preferably, the at least one binding agent can be at least temporarily bound to the support. For example, the binding agent is covalently bound to the support. Additionally, further assay components can be bound, e.g. covalently bound, to the support.

In alternative embodiments, the kit comprises a suitable detection device, which is capable of detecting a suitable reporter group of the compound, e.g. a dye, fluorogenic substrate or the like.

For example, the detection device comprises a light source (UV or vis), fluorescence, luminescence, a laser or the like.

Preferably, the kit comprises at least one suitable buffer component, e.g. a buffer premix, buffer solution or the like. As will be appreciated, the buffer component assists with sample preparation.

It may be of assistance to a user of the kit if the kit comprises a reference such as a colour card giving the range of the assay for guidance of acceptable or unacceptable clinical levels or the like.

Also provided is a product or device for specifically detecting active serine proteases, comprising a compound as hereinbefore and hereinafter described and a matrix to which the compound is permanently or semi-permanently attached, e.g. bound.

Particularly, the product may be a lateral flow device such as a dipstick, chip, membrane, plate or the like. In embodiments the product can comprise an absorbent pad, a test membrane, an immobilised antibody and a compound of the present invention wherein the absorbent pad is arranged to receive a test sample such that the test sample is brought into contact with a compound of the present invention such that if a protease being tested is present in the sample it can form a complex with the compound. The complex can then migrate through the device and bind to a conjugate with a detecting agent, for example streptavidin-colloidal gold. The expanded complex can then migrate through the device, for example typically by lateral flow. The expanded complex can then be bound by the immobilised antibody, for example immobilised antibody specific to the protease under investigation. Preferably binding of the complex by the immobilised antibody can be visualised in a test window. In preferred embodiments the product can further comprise an immobilised antibody with binding specificity to the reporter group of the compound or detecting agent of the conjugate.

In embodiments at least two compounds may be provided wherein at least two compounds have specificity to different proteases, for example a first compound with specificity to elastase and a second compound with specificity to chymotrypsin or trypsin like proteases.

In embodiments of the invention, an assay system or kit comprising a compound of the invention can be a lateral flow device or dipstick. Such embodiments may suitably be formed for use in a point of care assay to assist with patient management or as a home testing kit for personal disease management and monitoring.

As described above, in some embodiments of the present invention, the compound of and for use in the invention is not cell permeable. Permeability may be assessed using any assay method known to the skilled person. For example, the cell impermeability of a compound of interest may be assessed by comparing total cellular proteolytic activity in whole cell lysates after treatment with the compound of interest, e.g. for two hours, with total cellular proteolytic activity in whole cell lysates which have been incubated with the compound of interest post solubilisation in lysis buffer. The lysate samples may be incubated with one or more fluorogenic substrates to assess enzymatic activity. The fluorogenic substrate may be any suitable substrate for the compounds of interest. For example, the fluorogenic substrate may be a substrate for trypsin-like enzymes, and furin like enzymes or for prostasin/matriptase like enzymes. For example, substrates which may be used include Z-Gly-Gly-Arg-NH$_2$Mec (for general trypsin-like enzymes), p-Glu-Arg-Thr-Lys-Arg-NH$_2$Mec (for furin-like enzymes) and Boc-Gln-Ala-Arg-NH$_2$Mec (for prostasin/matriptase-like enzymes).

In some embodiments of the invention the compound of and for use in the invention does not inhibit thrombin/fibrin clot formation. Any suitable assay may be used by the skilled person to determine whether or not a compound of interest has such inhibitory activity. For example, fibrin clot formation may be determined in the presence or absence of an compound of interest using a turbimetric assay in which purified human fibrinogen is incubated in Tris-buffered saline (50 mM Tris/HCl, pH 7.4 containing 150 mM NaCl, and 2.5 mM CaCl$_2$) in the presence of thrombin to trigger clot formation with change in turbidity monitored for a period of time e.g. 1 h (A$_{405}$) at 37° C. and IC$_{50}$ values determined. The compound is considered not to inhibit fibrin clot formation if the determined IC$_{50}$ value is greater than a predetermined value, for example greater than 1 μM, for example greater than 5 μM, for example greater than 20 μM, such as greater than 50 μM.

The invention will now be described further in the following non-limiting examples with reference to the accompanying drawings in which.

Figure 9:
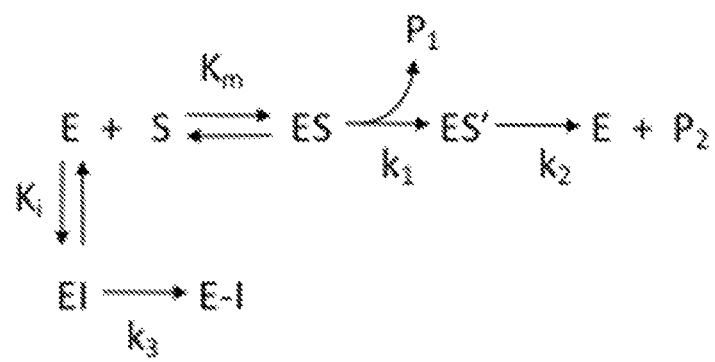

FIG. 9 shows a kinetic scheme for the irreversible inactivation of an enzyme by an inhibitor working through a complexing mechanism, in the presence of competing substrate. In this scheme, enzyme (E) and substrate (S) form a Michaelis complex (ES), prior to the formation of an acyl-enzyme intermediate (ES') with concomitant release of product ($P_1$). The formation of ES is characterised by $K_m$. Interconversion of ES into ES' is characterised by the first-order rate constant $k_1$. Hydrolysis of ES' regenerates E, with the concomitant formation of the second product $P_2$. This process is characterised by the rate constant $k_2$. In the presence of competing inhibitor (I), formation of the reversible enzyme-inhibitor complex (EI) is characterised by the inhibitor constant $K_i$. This is converted into the covalent/irreversible complex (E-I) characterised by a first-order rate constant $k_3$. The overall second-order rate constant for the inactivation of E by I is given by the ratio $k_3/K_i$.

Figure 11:
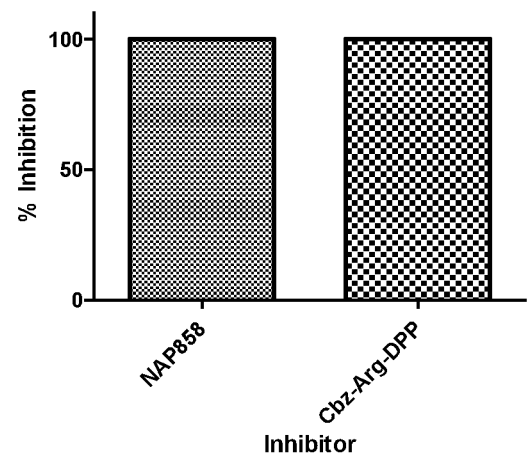
Figure 12:
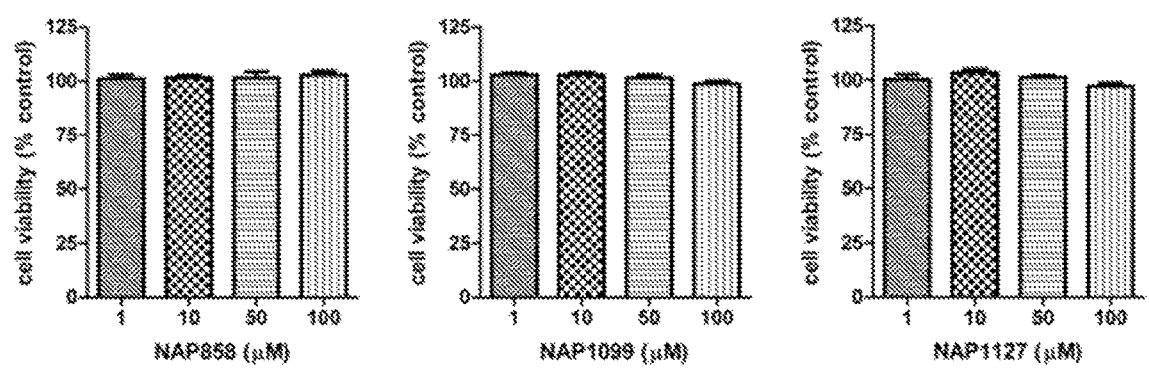
Figure 13:
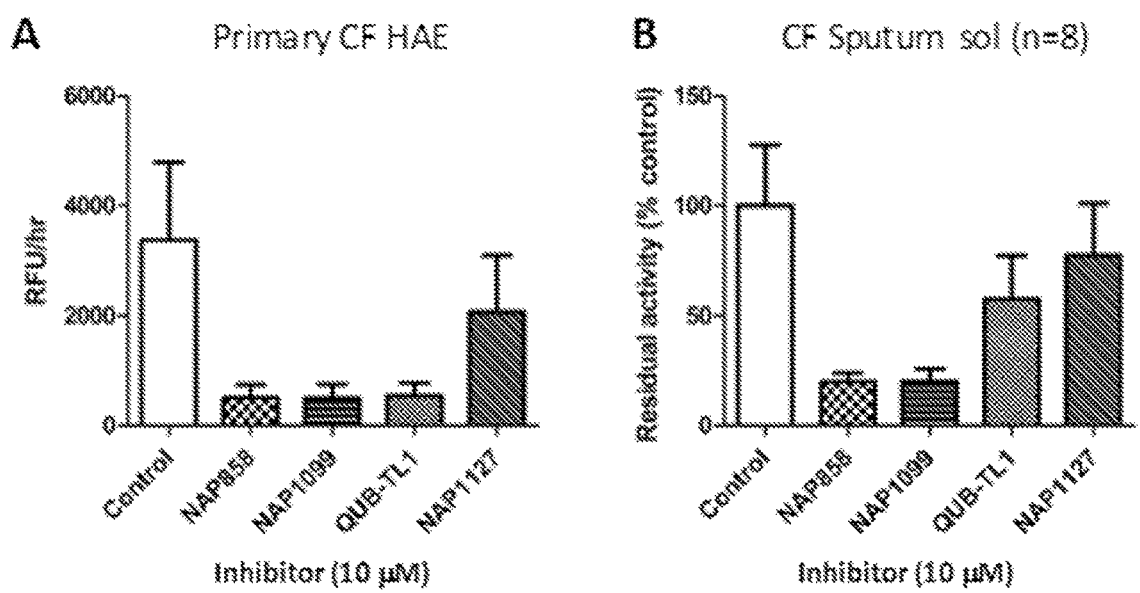
Figure 14:
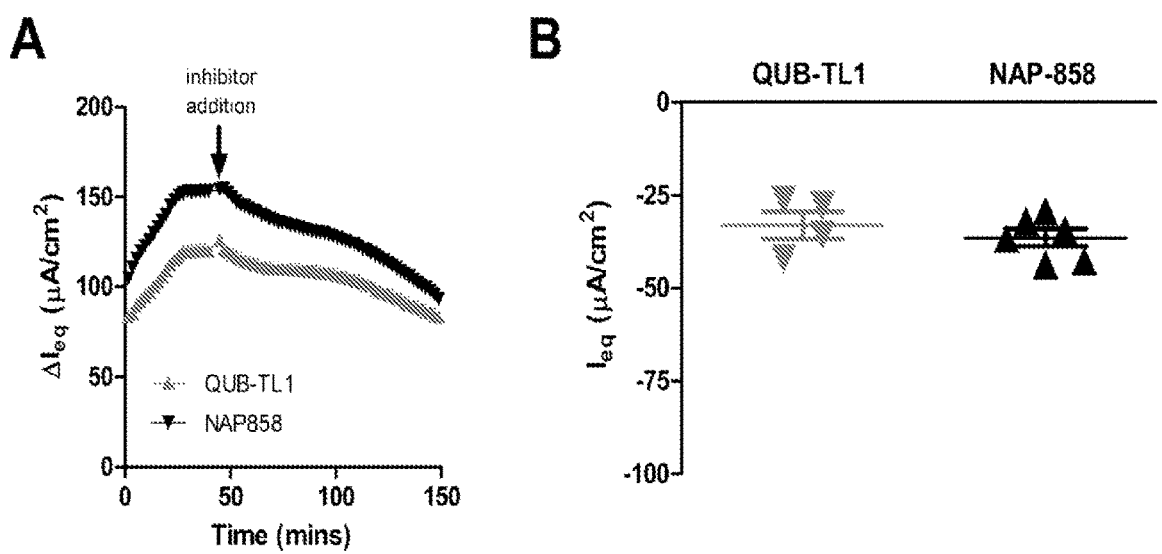
Figure 15A:
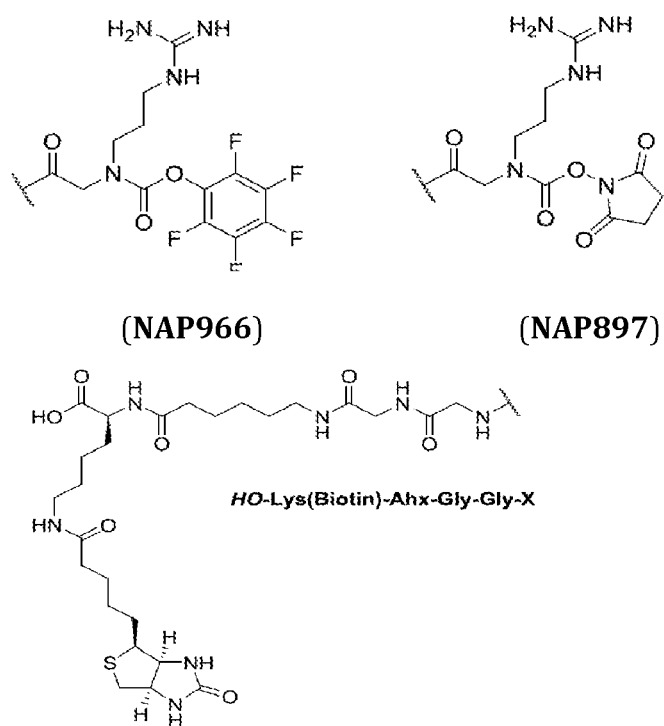
Figure 15B:
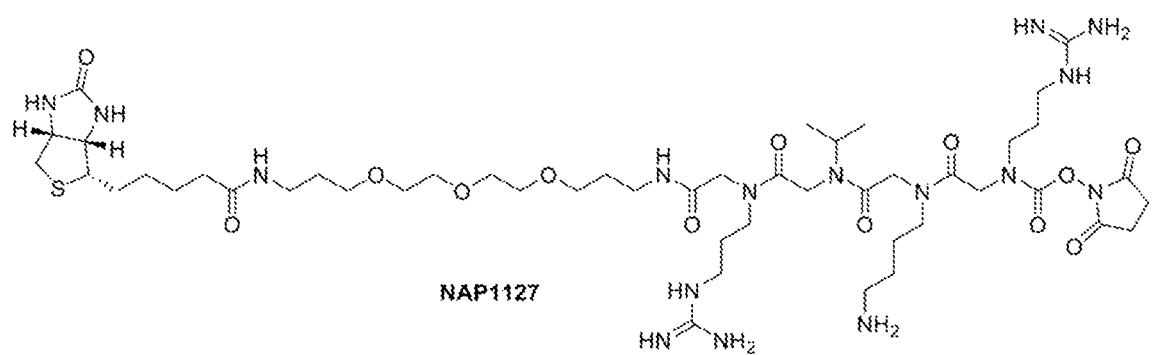
Figure 15C:
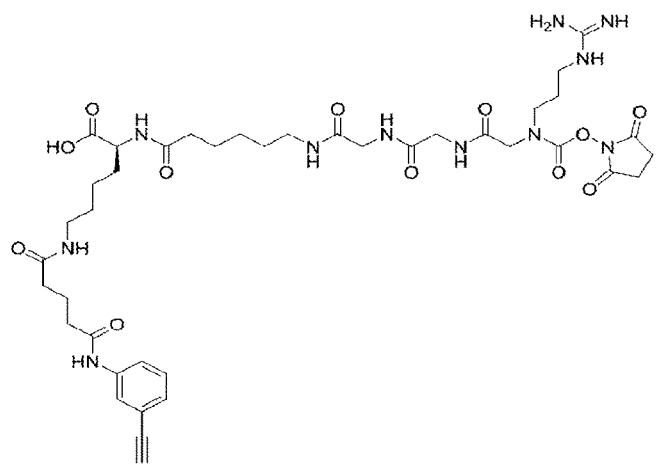
Figure 15D:
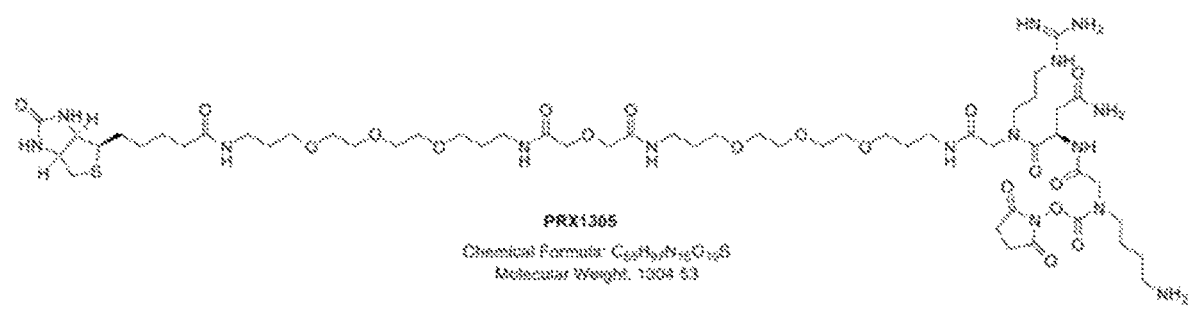
Figure 15E:
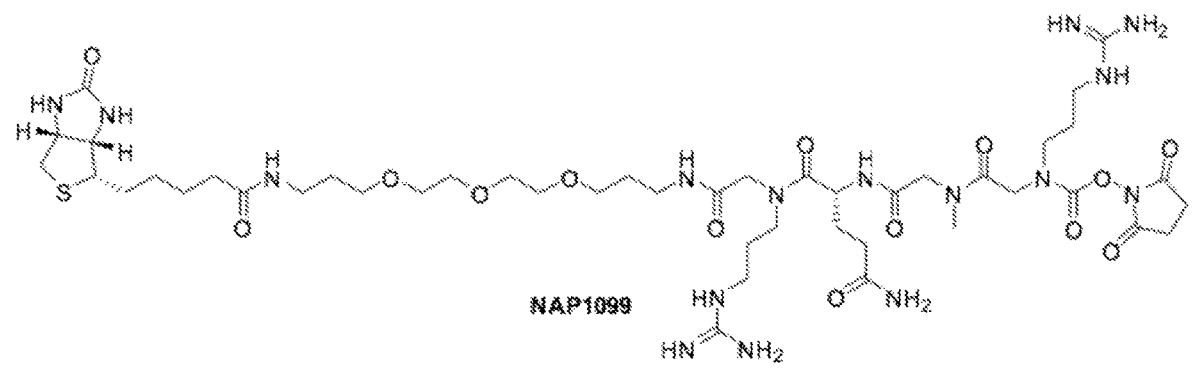

FIG. 10A illustrates the structure of QUB-TL1;

FIG. 10B shows a bar chart summarising the effect of serine protease inhibitors on mucociliary clearance (using primary cystic fibrosis airways epithelial cells grown at air-liquid interface); inhibitors (50 µM) were added for 24 hours, prior to analysis (n=3);

FIG. 11 illustrates a bar chart showing inhibition of trypsin-like serine proteases in CF sol against the Cbz-Gly-Gly-Arg-AMC substrate using NAP858 and Cbz-Arg-DPP;

FIG. 12 illustrates the results of cytotoxicity assays on the CF human airway epithelial cell line CuFi using three inhibitors;

FIG. 13 are bar charts illustrating the ability of compounds of the invention to inhibit tryptic activity using primary human airway epithelial (HAE) cell cultures (A) and sputum sol samples collected from 8 individual CF patients (B);

FIG. 14 illustrates inhibition of ENac activity in primary CF cultures using QUB-TL1 and NAP858;

FIG. 15A shows a comparison of structures of HO-Lys(Biotin)-Ahx-Gly-Gly-N-(n-guanidino-propyl)-glycine succinimidyl carbamate (NAP897) and HO-Lys(Biotin)-Ahx-Gly-Gly-N-(n-guanidino-propyl)-glycine pentafluorophenyl carbamate (NAP966);

FIG. 15B shows a schematic of structure of Biotin-PEG-NH—N-(n-guanidino-propyl)-glycine N(Val)-N(Lys)N-(n-guanidino-propyl)-glycine succinimidyl carbamate (NAP1127);

FIG. 15C shows a schematic of structure of N-6-(1-acetylene-3-amino-phenyl)-di-carboxy-pentane-Lys-NH-Ahx-NH-Gly-Gly-N-(n-guanidino-propyl)-glycine succinimidyl carbamate (NAP884);

FIG. 15D shows a schematic of structure of Biotinyl-$(PEG)_2$-N(Arg)-Asn-N-(n-amino-butyl)-glycine succinimidyl carbamate (PRX1305); and FIG. 15E shows a schematic of structure of Biotin-PEG-NArg-D-Gln-Sar-NArg-COOSu (NAP1099).

EXAMPLES

Figure 1:
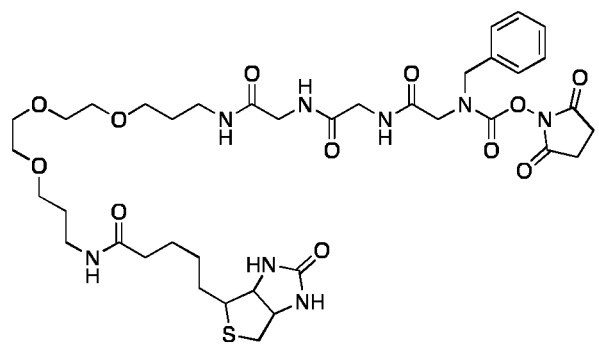
FIG. 1 illustrates the structure of Biotin-PEG-NH-Gly-Gly-N-(benzyl)-glycine succinimidyl carbamate (NAP849)
Figure 2:
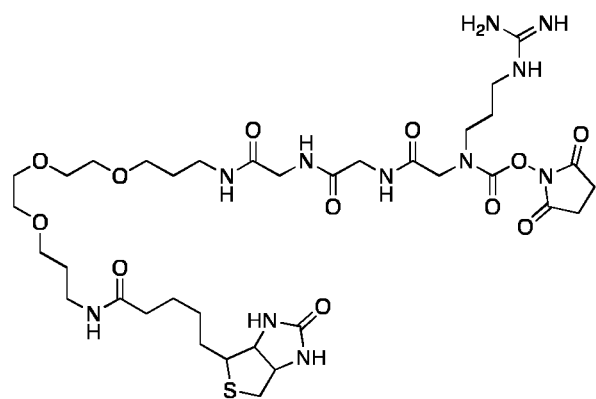
FIG. 2 illustrates the structure of Biotin-PEG-NH-Gly-Gly-N-(n-guanidino propyl)-glycine succinimidyl carbamate (NAP858)
Figure 3:
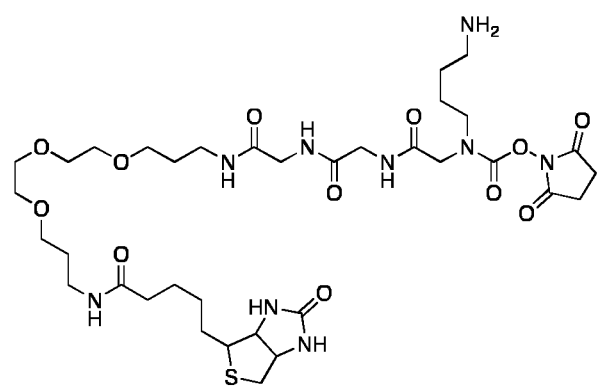
FIG. 3 illustrates the structure of Biotin-PEG-NH-Gly-Gly-N-(n-amino butyl)-glycine succinimidyl carbamate (NAP830)

Examples 1-3: Synthesis of Biotin-PEG-NH-Gly-Gly-N-(benzyl)-glycine succinimidyl carbamate, Biotin-PEG-NH-Gly-Gly-N-(n-guanidino-propyl)-glycine succinimidyl carbamate and Biotin-PEG-NH-Gly-Gly-N-(n-amino-butyl)-glycine succinimidyl carbamate Compounds of the invention, Biotin-PEG-NH-Gly-Gly-N-(benzyl)-glycine succinimidyl carbamate (FIG. 1), Biotin-PEG-NH-Gly-Gly-N-(n-guanidino-propyl)-glycine succinimidyl carbamate (FIG. 2), and Biotin-PEG-NH-Gly-Gly-N-(n-amino-butyl)-glycine succinimidyl carbamate (FIG. 3) were prepared according to the scheme shown in FIG. 6. Briefly, these compounds were synthesised utilising a solid-phase approach, on Biotin-PEG NovaTag resin (Novabiochem). This resin contains a Biotin-PEG-amine moiety linked through a BAL linker, forming an immobilised secondary amine, which can be reacted with activated carboxylic acids and amino acids to furnish the desired compounds. To this resin was coupled two glycine residues (Fmoc-Gly-OH) through standard coupling procedures, prior to coupling of the appropriate N-alkyl glycine residue. The corresponding Fmoc-protected N-alkyl glycine monomers Fmoc-N-(benzyl)-Gly-OH, Fmoc-N-(n-guanidino-propyl)-Gly-OH and Fmoc-N-(n-amino-butyl)-Gly-OH were available commercially (Polypeptide Group), which enabled these residues to be incorporated directly into the common peptidic core sequence, using standard Fmoc-SPPS protocols. After the incorporation of each of these Fmoc-protected N-alkyl glycine monomers into the target sequence, removal of the Fmoc-group was achieved using piperidine (20% v/v solution in DMF). The on-resin synthesis of the corresponding succinimidyl carbamates was achieved essentially according to the method of Niphakis et al. (2013). Briefly, a solution containing N,N'-disuccinimidyl carbonate (DSC) and 2,6-lutidine in anhydrous DCM/DMF (1:1) was added to each of the de-protected resins, in turn, until chloranil analysis indicated complete reaction of the terminal secondary $N^\alpha$ amine functions of each. The target peptides were then cleaved from the resin (and any side-chain-protecting group removed, simultaneously) using TFA/TIPS/DCM (95:2.5:2.5) and, following workup and precipitation in diethyl ether, the products were obtained in quantitative yield.

Figure 4:
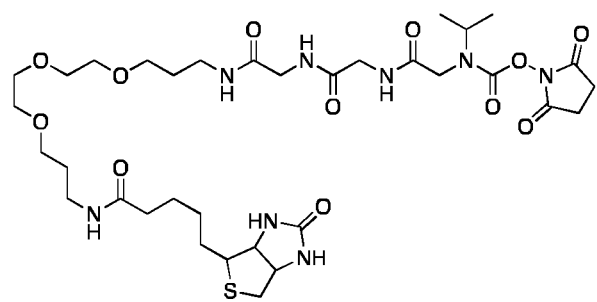
FIG. 4 illustrates the structure of Biotin-PEG-NH-Gly-Gly-N-(iso-propyl)-glycine succinimidyl carbamate (NAP800)
Figure 7:
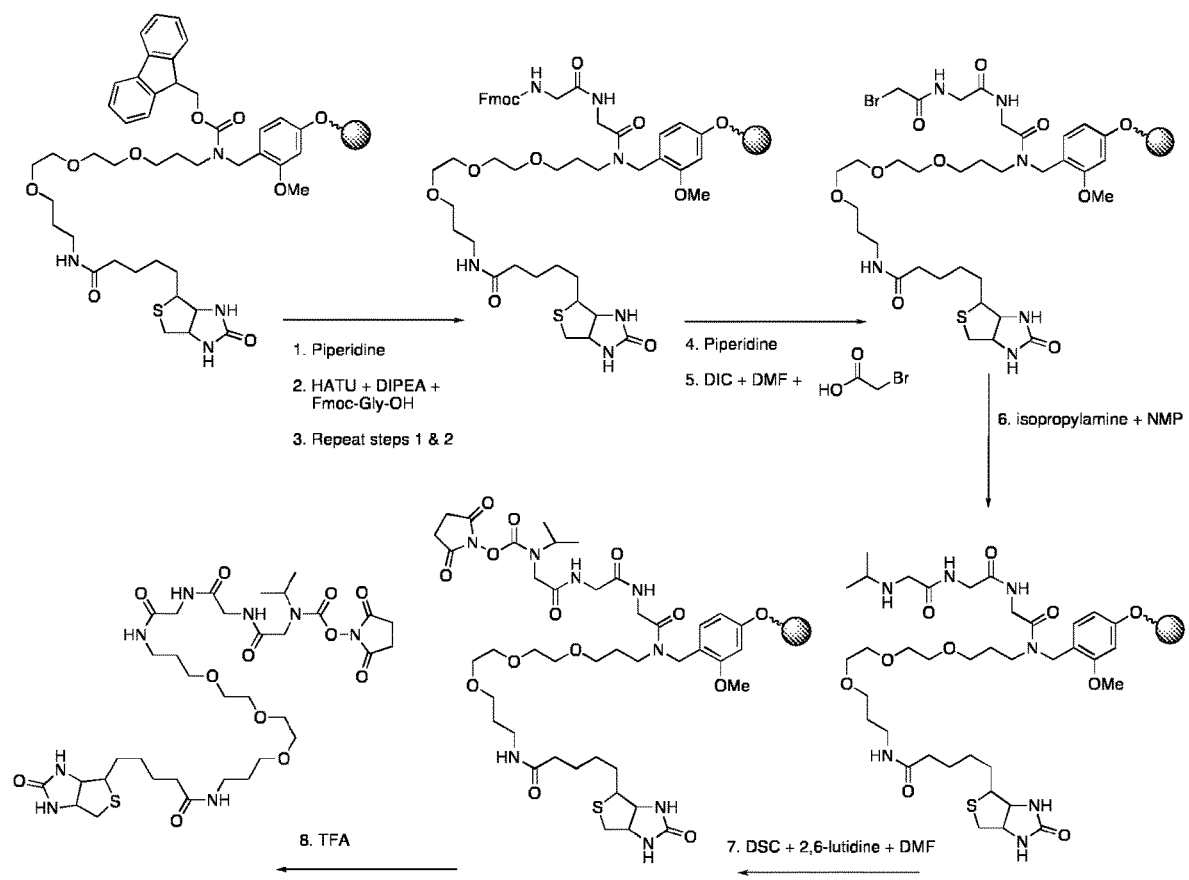
FIG. 7 illustrates a synthetic scheme for the solid phase synthesis of Biotin-PEG-NH-Gly-Gly-N-(iso-propyl)-glycine succinimidyl carbamate, illustrating the 'sub-monomer' approach for the on-resin construction of the N-alkyl glycine residue.

Example 4 Synthesis of Biotin-PEG-NH-Gly-Gly-N-(iso-propyl)-glycine succinimidyl carbamate A compound of the invention, Biotin-PEG-NH-Gly-Gly-N-(iso-propyl)-glycine succinimidyl carbamate (FIG. 4), was prepared according to the scheme shown in FIG. 7. Briefly, since the N-alkyl glycine residue Fmoc-N-(isopropyl)-Gly-OH, was not commercially available, an on-resin sub-monomer approach was followed. In essence, Botin-PEG-amine derivatised BAL resin was subjected to two coupling cycles with Fmoc-Gly-OH. The terminal Fmoc-group was then removed from the resin-tethered peptide and the primary amino function was bromoacetylated in a di-isopropyl-carbodiimide-mediated reaction, using a ten-fold excess of bromoacetic acid, essentially according to a previously reported method (Tran et al., 2011). This acylation step was repeated (4×30 minutes) with fresh reagents until Kaiser analysis indicated complete acylation. This was followed by the addition of a solution of isopropylamine in N-methylpyrrolidone (NMP) to allow displacement of the bromine group to form the desired secondary amine. Formation of the target succinimidyl carbamate and its subsequent cleavage was carried out described above for the other three analogues, to provide the required compound in excellent yield.

Example 5: Synthesis of Biotin-PEG-NH—N-(n-guanidino-propyl)-glycine -Gln-Sar-N-(n-guanidino-propyl)-glycine succinimidyl carbamate (NAP1099)

Figure 5:
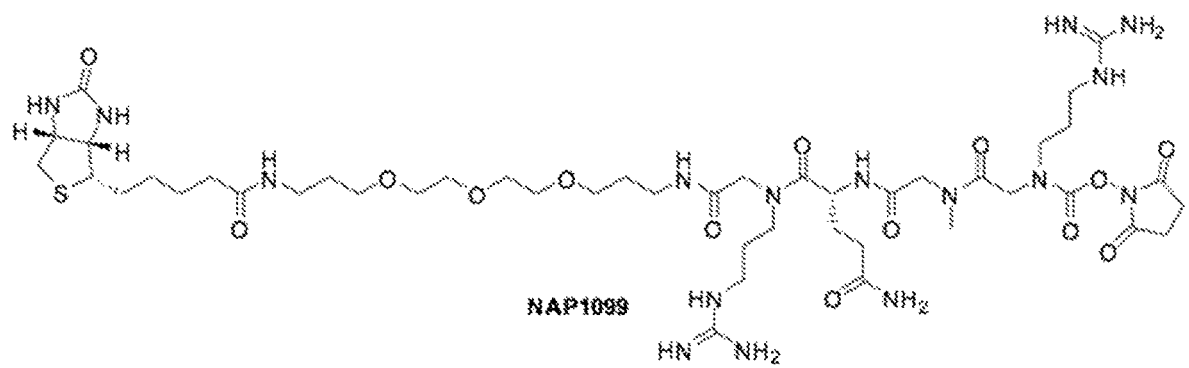
FIG. 5 illustrates the structure of Biotin-PEG-NH—N-(n-guanidino-propyl)-glycine-Gln-Sar-N-(n-guanidino-propyl)-glycine succinimidyl carbamate (NAP1099)
Figure 6:
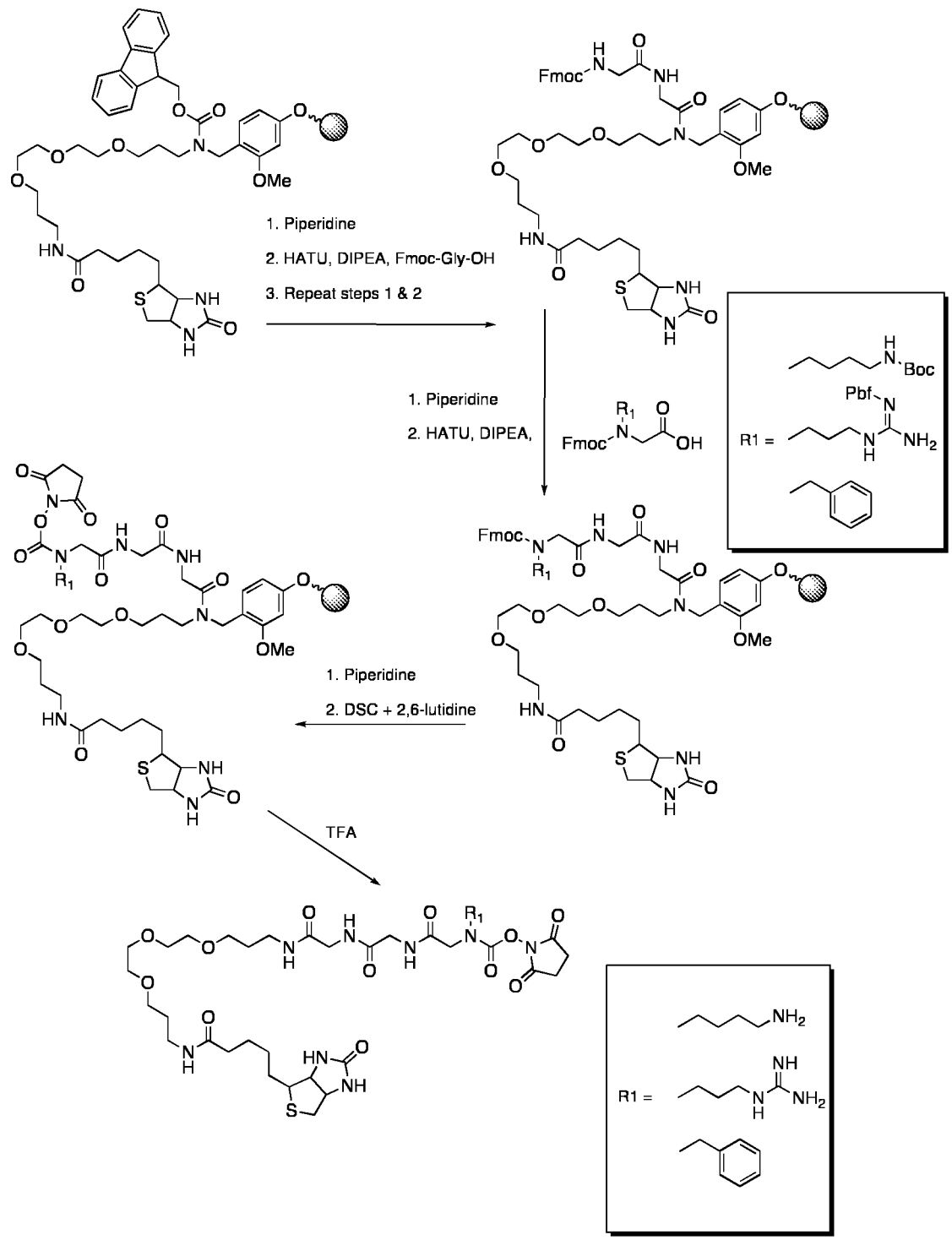
FIG. 6 illustrates a synthetic scheme for the solid phase synthesis of Biotin-PEG-NH-Gly-Gly-N-(benzyl)-glycine succinimidyl carbamate, Biotin-PEG-NH-Gly-Gly-N-(n-amino butyl)-glycine succinimidyl carbamate and Biotin-PEG-NH-Gly-Gly-N-(n-guanidinopropyl)-glycine succinimidyl carbamate, illustrating the use of preformed Fomc-N-alkyl glycine monomers.

Another compound of the invention, Biotin-PEG-NH—N-(n-guanidino-propyl)-glycine -Gln-Sar-N-(n-guanidino-propyl)-glycine succinimidyl carbamate (NAP1099) (FIG. 5) was synthesised according to the general Scheme illustrated in FIG. 6. The sarcosine, glutamine and N-(n-guanidino-propyl)-glycine residues were introduced as their N-Fmoc-protected derivatives, using standard coupling protocols.

Example 6: Inhibition Studies

Figure 8A:
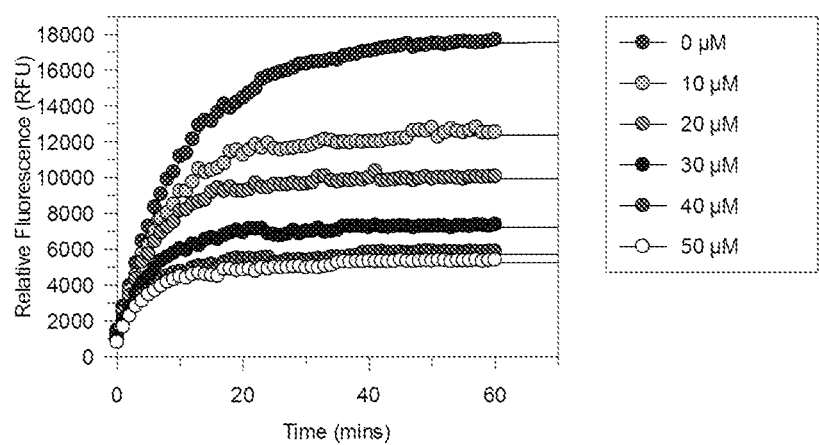
FIG. 8A illustrates progress curves for the inactivation of human neutrophil elastase by Biotin-PEG-NH-Gly-Gly-N-(iso-propyl)-glycine succinimidyl carbamate in the presence of competing fluorogenic substrate Boc-Val-Pro-Val-NH-Mec.
Figure 8B:
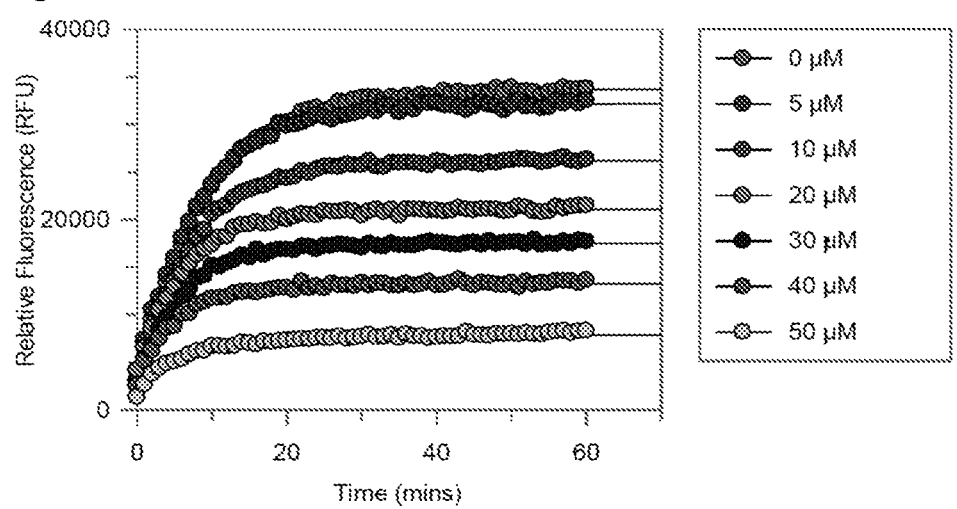
FIG. 8B illustrates progress curves for the inhibition of trypsin by (NAP966); all assays were carried out in PBS, pH 7.4, at 37° C., in the presence of varying concentrations of inhibitor (0.25-50 µM) and using a fixed substrate (Z-Gly-Gly-Arg-NHMec) concentration of 50 µM.
Figure 8C:
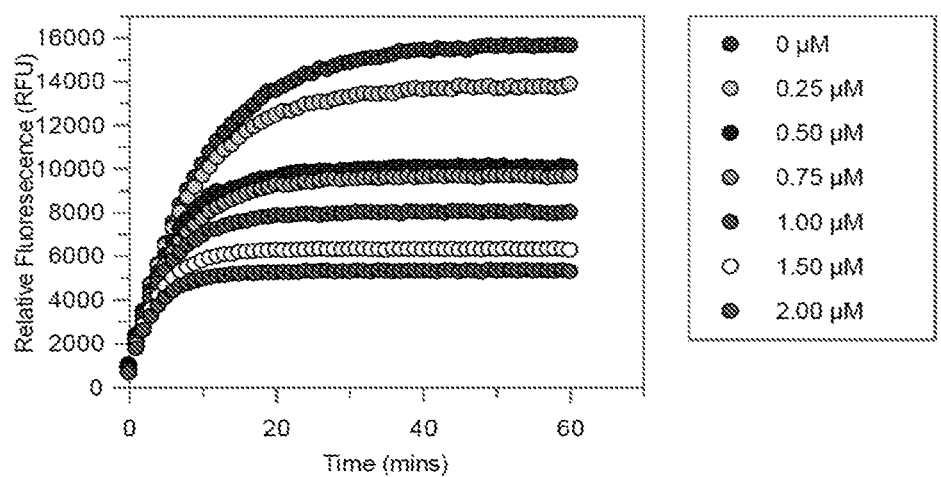
FIG. 8C illustrates progress curves for the inhibition of trypsin by (NAP897); all assays were carried out in PBS, pH 7.4, at 37° C., in the presence of varying concentrations of inhibitor (0.25-50 µM) and using a fixed substrate (Z-Gly-Gly-Arg-NHMec) concentration of 50 µM.
Figure 8D:
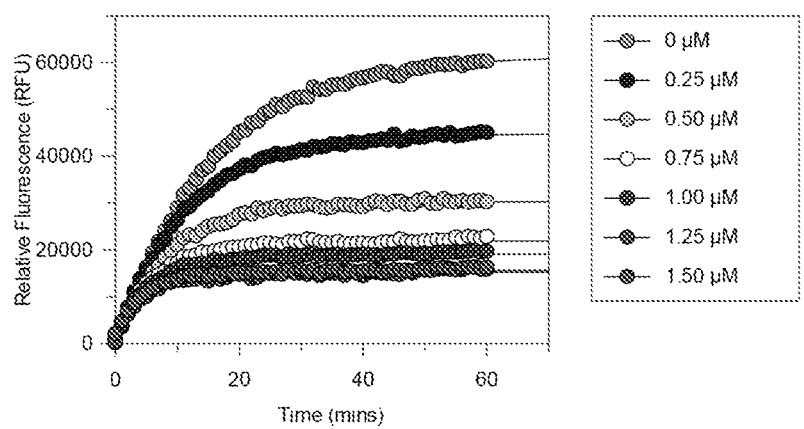
FIG. 8D illustrates progress curves for the inhibition of trypsin by (NAP884); all assays were carried out in PBS, pH 7.4, at 37° C., in the presence of varying concentrations of inhibitor (0.25-1.50 µM) and using a fixed substrate (Z-Gly-Gly-Arg-NHMec) concentration of 50 µM.
Figure 8E:
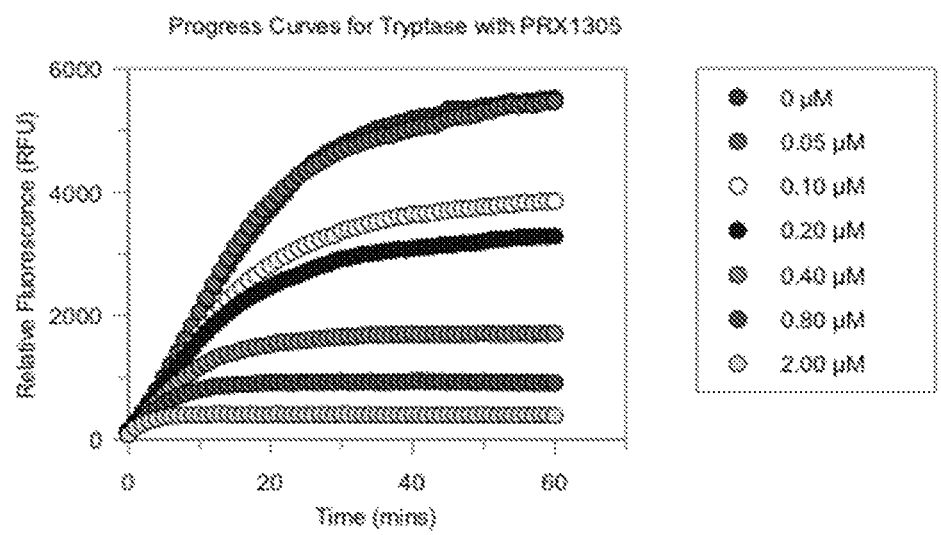
FIG. 8E illustrates progress curves for the inhibition of tryptase by (PRX1305)
Figure 8F:
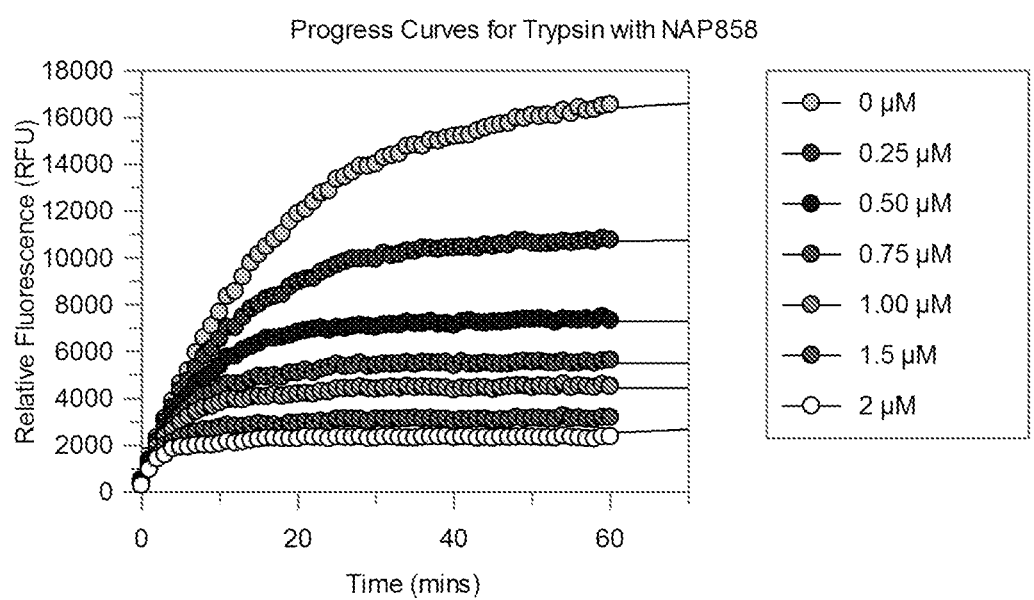
FIG. 8F illustrates progress curves for the inhibition of trypsin by (NAP858)

The ability of compounds of the invention to inhibit the activities of a range of commercially sourced proteases was assessed using steady state fluorogenic substrate assays. In essence, samples of each protease were added to PBS buffer, pH 7.4, maintained at 37° C., containing a fixed concentration of appropriate substrate (Suc-Ala-Ala-Pro-Phe-NH-Mec, chymotrypsin; MeO-Suc-Ala-Ala-Pro-Val-NHMec, Neutrophil Elastase; Cbz-Gly-Gly-Arg-NHMec, trypsin; Boc-Val-Pro-Arg-NHMec, thrombin; Boc-Val-Leu-Lys-NHMec, plasmin; all used at 50 µM) and varying concentrations (0.25-50 µM) of the N-alkyl glycine carbamate inhibitors. The final concentration of protease ranged from 0.05-0.3 µg/ml, depending on the activity of each. Progress curves were then generated by recording the increase in fluorescence as a function of time, for a period of between 30-60 minutes, using an excitation wavelength of 360 nm and emission wavelength of 485. FIG. 8A shows exemplar progress curves for neutrophil elastase-catalysed hydrolysis of MeO-Suc-Ala-Ala-Pro-Val-NHMec in the presence of varying concentrations of Biotin-PEG-NH-Gly-Gly-N-(iso-propyl)-glycine succinimidyl carbamate. Assays were carried out in PBS, pH 7.4, at 37° C., in the presence of varying concentrations of inhibitor (10-50 µM) and a fixed concentration of substrate (50 µM). Similar progress curves were obtained for other proteases and other inhibitors used in the study, (FIGS. 8B-8F). These progress curves are indicative of the action of an irreversible inhibitor working through a complexing mechanism shown in FIG. 9. In this mechanism, the inhibitor I, binds the target protease to form an initial reversible complex EI, characterised by the inhibitor constant $K_i$. This is followed by the formation of an irreversible complex E-I from EI, characterised by the first-order rate constant $k_3$. The overall second-order rate constant for the inactivation of the protease by the inhibitor is then given by the ratio $k_3/K_i$ (Walker and Elmore, 1984; Tian and Tsou, 1982).

The results of some of these inhibition studies are shown in Table 1. This records the kinetic parameters ($K_1$, $k_3$ and $k_3/K_i$) for the inactivation of the series of proteases utilised in the study with the various N-alkyl glycine carbamates.

TABLE 1

Inhibitory Kinetic Data

| | Inhibitor | Protease | $K_i$ (M) | $k_3$ (min$^{-1}$) | $k_3/K_i$ (M$^{-1}$ min$^{-1}$) |
|---|---|---|---|---|---|
| NAP858 | Biotin-PEG-NH-Gly-Gly-N-(n-guanidino-propyl)-glycine succinimidyl carbamate | Trypsin (n = 3) | 4.86 (±3.76) × 10$^{-7}$ | 0.299 (±0.037) | 1.95 (±2.62) × 10$^6$ |
| | | Matriptase (n = 3) | 7.33 (±0.10) × 10$^{-7}$ | 0.314 (±0.084) | 1.30 (±0.943) × 10$^6$ |
| | | Human Airways Trypsin-like protease (HAT) (n = 3) | 6.59 (±4.72) × 10$^{-7}$ | 0.464 (±0.164) | 1.50 (±1.76) × 10$^6$ |
| NKP830 | Biotin-PEG-NH-Gly-Gly-N-(n-amino-butyl)-glycine succinimidyl carbamate | Trypsin (n = 3) | 2.2 (±0.8) × 10$^{-7}$ | 0.5 (±0.1) | 2.7 (±0.5) × 10$^6$ |
| | | Plasmin (n = 2) | 7.2 (±0.3) × 10$^{-6}$ | 0.4 (±0.05) | 6.2 (±0.9) × 10$^4$ |
| NFP849 | Biotin-PEG-NH-Gly-Gly-N-(benzyl)-glycine succinimidyl carbamate | Chymotrypsin (n = 3) | 8.9 (±6.7) × 10$^{-7}$ | 0.8 (±0.3) | 1.3 (±0.4) × 10$^6$ |
| NVP800 | Biotin-PEG-NH-Gly-Gly-N-(iso-propyl)-glycine succinimidyl carbamate | Neutrophil Elastase (n = 2) | 6.0 (±1.4) × 10$^{-6}$ | 0.4 (±0.05) | 6.4 (±0.6) × 10$^4$ |
| NAT988 | Biotin-PEG-NH—(N-benzyl-glycyl)-(D)-phenylalanyl-N-(n-guanidino-propyl)-glycine succinimidyl carbamate | Thrombin (n = 2) | 8.8 (±2.5) × 10$^{-7}$ | 0.4 (±0 02) | 4.7 (± 1.1) × 10$^5$ |
| CG877 | Biotin-PEG-NH—(N-methyl glycyl)-(N-methyl glycyl)-N-(benzyl)-glycine succinimidyl carbamate | Chymotrypsin (n = 3) | 2.8 (±(n = 6) × 10$^{-6}$ | 0.7 (±(11) | 2.5 (±(922) × 10$^5$ |

TABLE 1-continued

Inhibitory Kinetic Data

| | Inhibitor | Protease | $K_i$ (M) | $k_3$ (min$^{-1}$) | $k_3/K_i$ (M$^{-1}$ min$^{-1}$) |
|---|---|---|---|---|---|
| NAP1099 | Biotin-PEG-NH—N-(n-guanidino-propyl)- | Trypsin (n = 3) | 1.50 (±1.26) × 10$^{-7}$ | 0.354 (±0.09) | 3.80 (±3.16) × 10$^6$ |
| | glycine-Gln-Sar-N-(n-guanidino-propyl)- | Matriptase (n = 3) | 8.33 (±7.84) × 10$^{-8}$ | 0.302 (±0.03) | 8.52 (±9.05) × 10$^6$ |
| | glycine succinimidyl carbamate | Human Airways Trypsin-like protease (HAT) (n = 3) | 3.22 (±4.23) × 10$^{-7}$ | 0.474 (±0.16) | 3.71 (±2.89) × 10$^6$ |
| NAP966 | | Trypsin (n = 3) | 2.1 (±0.3) × 10$^{-6}$ | 0.4 (±0.007) | 1.9 (±0.25) × 10$^5$ |
| NAP897 | | Trypsin (n = 3) | 6.6 (±4.1) × 10$^{-7}$ | 0.7 (±0.2) | 1.3 (±0.4) × 10$^6$ |
| NAP884 | | Trypsin (n = 3) | 4.20 (±1.11) × 10$^{-7}$ | 0.528 (±0.064) | 1.34 (±0.351) × 10$^6$ |

Mean (±SD);
n is the number of determinations

It can be appreciated from Table 1, that the series of N-alkyl glycine succinimidyl carbamates function as irreversible inhibitors of the serine proteases studied. For example, Biotin-PEG-NH-Gly-Gly-N-(n-guanidino-propyl)-glycine succinimidyl carbamate and Biotin-PEG-NH-Gly-Gly-N-(n-amino-butyl)-glycine succinimidyl carbamate, both of which contain a basic N-alkyl glycine carbamate moiety, function as potent inhibitors of trypsin, exhibiting virtually identical over all second-order rate constants of 2.60 (±0.884)×10$^6$M$^{-1}$·min$^{-1}$ and 2.74 (±0.547)×10$^6$M$^{-1}$·min$^{-1}$, respectively. Similarly, potent inhibition of chymotrypsin was obtained using Biotin-PEG-NH-Gly-Gly-N-(benzyl)-glycine succinimidyl carbamate, which inactivated this protease with a second-order rate constant of 1.28 (±0.442)×10$^6$ M$^{-1}$·min$^{-1}$. The replacement of the two glycine residues with two N-methyl-glycine residues to give Biotin-PEG-NH—(N-methyl glycyl)-(N-methyl glycyl)-N-(benzyl)-glycine succinimidyl carbamate, still provided an effective inhibitor of chymotrpsin, albeit with a reduced second-order rate constant of 2.46 (±0.214)×10$^5$ M$^{-1}$·min$^{-1}$, in comparison to that obtained for Biotin-PEG-NH-Gly-Gly-N-(benzyl)-glycine succinimidyl carbamate. This drop in effectiveness can be attributed to poorer $K_i$ and $k_3$ values for the former in comparison to the latter. The elastase-directed sequence Biotin-PEG-NH-Gly-Gly-N-(iso-propyl)-glycine succinimidyl carbamate functioned as an inhibitor of this protease exhibiting a second-order rate constant of 6.41 (±0.572)×10$^4$M$^{-1}$·min$^{-1}$. Although not as effective as the chymotrypsin or trypsin directed sequences against their respective targets, Biotin-PEG-NH-Gly-Gly-N-(iso-propyl)-glycine succinimidyl carbamate is an efficient inhibitor of elastase, since, for example, a 5 µM concentration will inactivate this protease with a $t_{1/2}$ of less than 2 minutes. Finally, the plasma trypsin-like serine proteases plasmin and thrombin were efficiently inhibited by the basic N-alkyl glycine carbamate sequences Biotin-PEG-NH-Gly-Gly-N-(n-amino-butyl)-glycine succinimidyl carbamate and Biotin-PEG-NH—(N-benzyl-glycyl)-(D)-phenylalanyl-N-(n-guanidino-propyl)-glycine succinimidyl carbamate, respectively.

Example 7—Biotin-PEG-NH-Gly-Gly-N-(n-guanidino-propyl)-glycine succinimidyl carbamate Enhances Mucociliary Clearance Mucociliary clearance was quantified by measuring the velocity of microbeads apically applied to differentiated primary CF Airway Epithelial Cells (AECs). Compounds (50 µM) were added to the apical surface of primary CF AECs for a period of 24 hours. Mucociliary flow was then determined by tracking and measuring the velocity of apically applied microbeads across the CF AEC surface. The effect of the compounds of the invention were compared to a vehicle only negative control and a positive control, QUB-TL1. The inventors have previously shown that QUB-TL1, the structure of which is shown in FIG. 10A, increases mucociliary clearance using primary CF AECs (Reihill et al, 2016). As shown in FIG. 10B, treatment of CF AECs by NAP858 (50 µM) for 24 hours resulted in markedly improved mucociliary clearance (from 3.5 (vehicle control) to 6.83 µm/s; n=3).

BIOLOGICAL EXAMPLES

Example 8 NAP858 Inhibits Trypsin-Like Serine Proteases in CF Sputum Sol

The inventors investigated the effect of compounds of the invention on biological samples using sol from patients with cystic fibrosis and cystic fibrosis cell lines.

FIG. 11 illustrates that NAP858 causes complete inhibition of the hydrolytic action of trypsin-like serine proteases in CF Sol as determined by inhibition of hydrolysis of the substrate, Cbz-Gly-Gly-Arg-AMC. Briefly, the spectrofluorimetic analysis was conducted on a sample of pooled supernatant recovered by centrifugation from expectorated cystic fibrosis sputum, which had been diluted ×4 with phosphate-buffered saline (sputum sol). Samples were treated in duplicate with NAP858 (10 µM) and a control compound, Cbz-Arg-diphenylphosphonate (Cbz-Arg-DPP) (10 µM). The rate of hydrolysis of the substrate at 37° C. was monitored and inhibition as a % of an untreated control calculated.

Example 9 Cytotoxicity

The inventors performed cytotoxicity assays on cells of the human CuFi cell line. Briefly, CuFi cells (a CF human epithelial cell line) were treated for 24 hours with NAP858, NAP1099, and NAP1127 over a ranged of concentrations (1-100 µM), before the addition of MTS tetrazolium compound (Abcam). MIS Cell Proliferation Assay Kit is a colorimetric method for sensitive quantification of viable cells in proliferation and cytotoxicity assay. The assay is based on the reduction of MIS tetrazolium compound by viable cells to generate a colored formazan product that is soluble in cell culture media. This conversion is thought to be carried out by NAD(P)H-dependent dehydrogenase enzymes in metabolically active cells. The formazan dye produced by viable cells can be quantified by measuring the absorbance at 490-500 nm. As shown in FIG. 12, each of the inhibitors tested were well tolerated.

Example 10 Inhibition of Endogenous Protease Activity

The ability of compounds of the invention to inhibit extracellular (apical surface) tryptic activity was investigated using primary human airway epithelial (HAE) cell cultures (A) and sputum sol samples collected from 8 individual CF patients (B). Briefly, HAE cells grown to confluence on 96-well plates were treated with a range of compounds (NAP858, NAP1099, NAP 1127 and QUB-TL1; all at 10 µM) and the rate of hydrolysis of Boc-QAR-AMC (50 µM) determined at 37° C. Inhibition of endogenous protease activities in CF sputum sol, was conducted as for Example 8 but in the presence of Boc-Gln-Ala-Arg-AMC (50 µM) as substrate. The rate of hydrolysis of the substrate at 37° C. was monitored and residual activity determined. In primary HAE NAP858 and NAP1099 reduced extracellular tryptic activity to a similar degree as that of QUB-TL1 (FIG. 13A). Further FIG. 13B shows that NAP858, and NAP1099 were superior to QUB-TL1 when incubated with CF sputum sol.

Example 11 Effect of NAP858 on ENac Activity

The effect of compounds of the invention on ENaC current was investigated. ENaC-expressing FRT cells were treated with QUB-TL1 or NAP858 (50 µM) for ~45 mins and Ieq measured. The experiment was terminated by the addition of amiloride (10 µM) which inhibited >95% of the observable current. All determinations were conducted using a TECC24 semiautomated system. Unlike the traditional Ussing chamber assays, where the short circuit current ($I_{SC}$) is measured as an index of CFTR correction, the TECC-24 assay measures the equivalent current ($I_{EQ}$). The TECC-24 assay format offers some advantages over the Ussing chamber assay, one of which is the higher throughput; the other involves the ability to measure the $I_{EQ}$ with the test compounds continuously present in the recording medium.

As shown in FIG. 14, NAP-858 reduced ENaC activity in primary CF cultures to a similar degree as QUB-TL1 (36 vs 33 µA/cm2) over a 90 minute period.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

REFERENCE LIST

1. Gibson, R. L., Burns, J. L., & Ramsey, B. W. Pathophysiology and management of pulmonary infections in cystic fibrosis. *Am. J. Respir. Crit Care Med.* 168, 918-951 (2003).
2. Donaldson, S. H. & Boucher, R. C. Sodium channels and cystic fibrosis. *Chest* 132, 1631-1636 (2007).
3. Boucher, R. C., Cotton, C. U., Gatzy, J. T., Knowles, M. R., & Yankaskas, J. R. Evidence for reduced Cl- and increased Na+ permeability in cystic fibrosis human primary cell cultures. *J. Physiol* 405, 77-103 (1988).
4. Stutts, M. J. et al. CFTR as a cAMP-dependent regulator of sodium channels. *Science* 269, 847-850 (1995).
5. Boucher, R. C. Airway surface dehydration in cystic fibrosis: pathogenesis and therapy. *Annu. Rev. Med.* 58, 157-170 (2007).
6. Sheng, S., Carattino, M. D., Bruns, J. B., Hughey, R. P., & Kleyman, T. R. Furin cleavage activates the epithelial Na+ channel by relieving Na+ self-inhibition. *Am. J. Physiol Renal Physiol* 290, F1488-F1496 (2006).
7. Kleyman, T. R., Carattino, M. D., & Hughey, R. P. ENaC at the cutting edge: regulation of epithelial sodium channels by proteases. *J. Biol. Chem.* 284, 20447-20451 (2009).
8. Bruns, J. B. et al. Epithelial Na+ channels are fully activated by furin- and prostasin-dependent release of an inhibitory peptide from the gamma-subunit. *J. Biol. Chem.* 282, 6153-6160 (2007).
9. Nimishakavi, S. et al. Activity and inhibition of prostasin and matriptase on apical and basolateral surfaces of human airway epithelial cells. *Am. J. Physiol Lung Cell Mol. Physiol* 303, L97-106 (2012).
10. Myerburg, M. M. et al. Prostasin expression is regulated by airway surface liquid volume and is increased in cystic fibrosis. *Am. J. Physiol Lung Cell Mol. Physiol* 294, L932-L941 (2008).
11. Ornatowski, W., Poschet, J. F., Perkett, E., Taylor-Cousar, J. L., & Deretic, V. Elevated furin levels in human cystic fibrosis cells result in hypersusceptibility to exotoxin A-induced cytotoxicity. *J. Clin. Invest* 117, 3489-3497 (2007).
12. Tong, Z., Illek, B., Bhagwandin, V. J., Verghese, G. M., & Caughey, G. H. Prostasin, a membrane-anchored serine peptidase, regulates sodium currents in JME/CF15 cells, a cystic fibrosis airway epithelial cell line. *Am. J. Physiol Lung Cell Mol. Physiol* 287, L928-L935 (2004).
13. Coote, K. et al. Camostat attenuates airway epithelial sodium channel function in vivo through the inhibition of a channel-activating protease. *J. Pharmacol. Exp. Ther.* 329, 764-774 (2009).
14. Rowe, S. M. et al. Reduced sodium transport with nasal administration of the prostasin inhibitor camostat in subjects with cystic fibrosis. *Chest* 144, 200-207 (2013).
15. Myerburg, M. M., Harvey, P. R., Heidrich, E. M., Pilewski, J. M., & Butterworth, M. B. Acute regulation of the epithelial sodium channel in airway epithelia by proteases and trafficking. *Am. J. Respir. Cell Mol. Biol.* 43, 712-719 (2010).
16. Dubois, C. M. et al. Evidence that furin is an authentic transforming growth factor-beta1-converting enzyme. *Am. J. Pathol.* 158, 305-316 (2001).
17. Arkwright, P. D. et al. TGF-beta(1) genotype and accelerated decline in lung function of patients with cystic fibrosis. *Thorax* 55, 459-462 (2000).
18. Gaggar, A. et al. The role of matrix metalloproteinases in cystic fibrosis lung disease. *Eur. Respir. J.* 38, 721-727 (2011).
19. Ra, H. J. & Parks, W. C. Control of matrix metalloproteinase catalytic activity. *Matrix Biol.* 26, 587-596 (2007).
20. Stieneke-Grober, A. et al. Influenza virus hemagglutinin with multibasic cleavage site is activated by furin, a subtilisin-like endoprotease. *EMBO J.* 11, 2407-2414 (1992).
21. Ortiz, J. R. et al. Influenza-associated cystic fibrosis pulmonary exacerbations. *Chest* 137, 852-860 (2010).

22. Inocencio, N. M., Moehring, J. M., & Moehring, T. J. Furin activates *Pseudomonas* exotoxin A by specific cleavage in vivo and in vitro. *J. Biol. Chem.* 269, 31831-31835 (1994).
23. Ogata, M., Chaudhary, V. K., Pastan, I., & FitzGerald, D. J. Processing of *Pseudomonas* exotoxin by a cellular protease results in the generation of a 37,000-Da toxin fragment that is translocated to the cytosol. *J. Biol. Chem.* 265, 20678-20685 (1990).
24. Jaffar-Bandjee, M. C. et al. Production of elastase, exotoxin A, and alkaline protease in sputa during pulmonary exacerbation of cystic fibrosis in patients chronically infected by *Pseudomonas aeruginosa*. *J. Clin. Microbiol.* 33, 924-929 (1995).
25. Yasuoka, S. et al. Purification, characterization, and localization of a novel trypsin-like protease found in the human airway. *Am. J. Respir. Cell Mol. Biol.* 16, 300-308 (1997).
26. Chokki, M. et al. Human airway trypsin-like protease increases mucin gene expression in airway epithelial cells. *Am. J. Respir. Cell Mol. Biol.* 30, 470-478 (2004).
27. Matsushima, R. et al. Human airway trypsin-like protease stimulates human bronchial fibroblast proliferation in a protease-activated receptor-2-dependent pathway. *Am. J. Physiol Lung Cell Mol. Physiol* 290, L385-L395 (2006).
28. Liu, C., Li, Q., Zhou, X., Kolosov, V. P., & Perelman, J. M. Human airway trypsin-like protease induces mucin-SAC hypersecretion via a protease-activated receptor 2-mediated pathway in human airway epithelial cells. *Arch. Biochem. Biophys.* 535, 234-240 (2013).
29. Donaldson, S. H. et al. Regulation of the epithelial sodium channel by serine proteases in human airways. *J. Biol. Chem.* 277, 8338-8345 (2002).
30. Adebamiro, A., Cheng, Y., Johnson, J. P., & Bridges, R. J. Endogenous protease activation of ENaC: effect of serine protease inhibition on ENaC single channel properties. *J. Gen. Physiol* 126, 339-352 (2005).
31. Vallet, V., Chraibi, A., Gaeggeler, H. P., Horisberger, J. D., & Rossier, B. C. An epithelial serine protease activates the amiloride-sensitive sodium channel. *Nature* 389, 607-610 (1997).
32. Molloy, S. S., Bresnahan, P. A., Leppla, S. H., Klimpel, K. R., & Thomas, G. Human furin is a calcium-dependent serine endoprotease that recognizes the sequence Arg-X-X-Arg and efficiently cleaves anthrax toxin protective antigen. *J. Biol. Chem.* 267, 16396-16402 (1992).
33. Cravatt, B. F., Wright, A. T., & Kozarich, J. W. Activity-based protein profiling: from enzyme chemistry to proteomic chemistry. *Annu. Rev. Biochem.* 77, 383-414 (2008).
34. Kay, G., Bailie, J. R., Halliday, I. M., Nelson, J., & Walker, B. The synthesis, kinetic characterization and application of biotinylated aminoacylchloromethanes for the detection of chymotrypsin and trypsin-like serine proteinases. *Biochem. J.* 283 (Pt 2), 455-459 (1992).
35. Cullen, B. M., Halliday, I. M., Kay, G., Nelson, J., & Walker, B. The application of a novel biotinylated affinity label for the detection of a cathepsin B-like precursor produced by breast-tumour cells in culture. *Biochem. J.* 283 (Pt 2), 461-465 (1992).
36. McGinty, A., Moore, M., Halton, D. W., & Walker, B. Characterization of the cysteine proteinases of the common liver fluke *Fasciola hepatica* using novel, active-site directed affinity labels. *Parasitology* 106 (Pt 5), 487-493 (1993).
37. Gilmore, B. F. et al. Synthesis, kinetic evaluation, and utilization of a biotinylated dipeptide proline diphenyl phosphonate for the disclosure of dipeptidyl peptidase IV-like serine proteases. *Biochem. Biophys. Res. Commun.* 347, 373-379 (2006).
38. Gilmore, B. F. et al. Expedited solid-phase synthesis of fluorescently labeled and biotinylated aminoalkane diphenyl phosphonate affinity probes for chymotrypsin- and elastase-like serine proteases. *Bioconjug. Chem.* 20, 2098-2105 (2009).
39. Walker B & McGinty A Detection and labelling of proteases using biotinylated active site-directed affinity labels (ed. Celis J. E.) 351-357 (Academic Press, 1998).
40. Tian, W. X. & Tsou, C. L. Determination of the rate constant of enzyme modification by measuring the substrate reaction in the presence of the modifier. *Biochemistry* 21, 1028-1032 (1982).
41. Walker, B. & Elmore, D. T. The irreversible inhibition of urokinase, kidney-cell plasminogen activator, plasmin and beta-trypsin by 1-(N-6-amino-n-hexyl)carbamoylimidazole. *Biochem. J.* 221, 277-280 (1984).
42. Zabner, J. et al. Development of cystic fibrosis and noncystic fibrosis airway cell lines. *Am. J. Physiol Lung Cell Mol. Physiol* 284, L844-L854 (2003).
43. Hallenberger, S. et al. Inhibition of furin-mediated cleavage activation of HIV-1 glycoprotein gp160. *Nature* 360, 358-361 (1992).
44. Kohler, D., App, E., Schmitz-Schumann, M., Wurtemberger, G., & Matthys, H. Inhalation of amiloride improves the mucociliary and the cough clearance in patients with cystic fibroses. *Eur. J. Respir. Dis.* Suppl146, 319-326 (1986).
45. App, E. M., King, M., Helfesrieder, R., Kohler, D., & Matthys, H. Acute and long-term amiloride inhalation in cystic fibrosis lung disease. A rational approach to cystic fibrosis therapy. *Am. Rev. Respir. Dis.* 141, 605-612 (1990).
46. Hirsh, A. J. et al. Evaluation of second generation amiloride analogs as therapy for cystic fibrosis lung disease. *J. Pharmacol. Exp. Ther.* 311, 929-938 (2004).
47. Coakley, R. D. et al. Abnormal surface liquid pH regulation by cultured cystic fibrosis bronchial epithelium. *Proc. Natl. Acad. Sci. U. S. A* 100, 16083-16088 (2003).
48. Pezzulo, A. A. et al. Reduced airway surface pH impairs bacterial killing in the porcine cystic fibrosis lung. *Nature* 487, 109-113 (2012).
49. Verghese, G. M., Gutknecht, M. F., & Caughey, G. H. Prostasin regulates epithelial monolayer function: cell-specific Gpld1-mediated secretion and functional role for GPI anchor. *Am. J. Physiol Cell Physiol* 291, C1258-C1270 (2006).
50. Oberst, M. D. et al. Characterization of matriptase expression in normal human tissues. *J. Histochem. Cytochem.* 51, 1017-1025 (2003).
51. Wang, J. K. et al. Polarized epithelial cells secrete matriptase as a consequence of zymogen activation and HAI-1-mediated inhibition. *Am. J. Physiol Cell Physiol* 297, C459-C470 (2009).
52. Friis, S. et al. A matriptase-prostasin reciprocal zymogen activation complex with unique features: prostasin as a non-enzymatic co-factor for matriptase activation. *J. Biol. Chem.* 288, 19028-19039 (2013).
53. Vallet, V., Pfister, C., Loffing, J., & Rossier, B. C. Cell-surface expression of the channel activating protease xCAP-1 is required for activation of ENaC in the *Xenopus* oocyte. *J. Am. Soc. Nephrol.* 13, 588-594 (2002).

54. Iwakiri, K. et al. Human airway trypsin-like protease induces PAR-2-mediated IL-8 release in psoriasis vulgaris. *J. Invest Dermatol.* 122, 937-944 (2004).
55. Beaulieu, A. et al. Matriptase proteolytically activates influenza virus and promotes multicycle replication in the human airway epithelium. *J. Virol.* 87, 4237-4251 (2013).
56. Johansen, H. K. & Hoiby, N. Seasonal onset of initial colonisation and chronic infection with *Pseudomonas aeruginosa* in patients with cystic fibrosis in Denmark. *Thorax* 47, 109-111 (1992).
57. Hughey, R. P. et al. Epithelial sodium channels are activated by furin-dependent proteolysis. *J. Biol. Chem.* 279, 18111-18114 (2004).
58. Hughey, R. P., Carattino, M. D., & Kleyman, T. R. Role of proteolysis in the activation of epithelial sodium channels. *Curr. Opin. Nephrol. Hypertens.* 16, 444-450 (2007).
59. Liu, P. V. Extracellular toxins of *Pseudomonas aeruginosa*. *J. Infect. Dis.* 130 Suppl, S94-S99 (1974).
60. Miyazaki, S., Matsumoto, T., Tateda, K., Ohno, A., & Yamaguchi, K. Role of exotoxin A in inducing severe *Pseudomonas aeruginosa* infections in mice. *J. Med. Microbiol.* 43, 169-175 (1995).
61. Woods, D. E., Cryz, S. J., Friedman, R. L., & Iglewski, B. H. Contribution of toxin A and elastase to virulence of *Pseudomonas aeruginosa* in chronic lung infections of rats. *Infect. Immun.* 36, 1223-1228 (1982).
62. Klinger, J. D., Straus, D. C., Hilton, C. B., & Bass, J. A. Antibodies to proteases and exotoxin A of *Pseudomonas aeruginosa* in patients with cystic fibrosis: Demonstration by radioimmunoassay. *J. Infect. Dis.* 138, 49-8 (1978).
63. Cross, A. S., Sadoff, J. C., Iglewski, B. H., & Sokol, P. A. Evidence for the role of toxin A in the pathogenesis of infection with *Pseudomonas aeruginosa* in humans. *J. Infect. Dis.* 142, 538-546 (1980).
64. Kounnas, M. Z. et al. The alpha 2-macroglobulin receptor/low density lipoprotein receptor-related protein binds and internalizes *Pseudomonas* exotoxin A. *J. Biol. Chem.* 267, 12420-12423 (1992).
65. Gu, M., Gordon, V. M., FitzGerald, D. J., & Leppla, S. H. Furin regulates both the activation of *Pseudomonas* exotoxin A and the Quantity of the toxin receptor expressed on target cells. *Infect. Immun.* 64, 524-527 (1996).
66. Schidlow, D. V., Taussig, L. M., & Knowles, M. R. Cystic Fibrosis Foundation consensus conference report on pulmonary complications of cystic fibrosis. *Pediatr. Pulmonol.* 15, 187-198 (1993).
67. Mentz, W. M. et al. Deposition, clearance, and effects of aerosolized amiloride in sheep airways. *Am. Rev. Respir. Dis.* 134, 938-943 (1986).
68. Hirsh, A. J. Altering airway surface liquid volume: inhalation therapy with amiloride and hyperosmotic agents. *Adv. Drug Deliv. Rev.* 54, 1445-1462 (2002).
69. Noone, P. G. et al. Airway deposition and clearance and systemic pharmacokinetics of amiloride following aerosolization with an ultrasonic nebulizer to normal airways. *Chest* 112, 1283-1290 (1997).
70. Niphakis, M J., Cognetta, A B., Chang J W., Matthew W. Buczynski, M W., Parsons, L H., Byrne, F., Burston, Victoria Chapman, V., Cravatt, B F. Evaluation of NHS Carbamates as a Potent and Selective Class of Endocannabinoid Hydrolase Inhibitors. ACS Chem. Neurosci., 4, 1322-1332 (2013).
71. Tran, H., Gael, S. L., Connolly, M. D., Zuckermann, R. N. Solid-phase Submonomer Synthesis of Peptoid Polymers and their Self-Assembly into Highly-Ordered Nanosheets. *J. Vis. Exp.* 57, e3373, doi:10.3791/3373 (2011).
72. Reihill, J A, Walker B, Hamilton R A, Ferguson T E G, Maye J R, Elborn J S, Stutts M J, Harvey B J, Saint-Criq V, Hendrick S and Martin S L. (2016a) Inhibition of Protease-Epithelial Sodium Channel Signaling Improves Mucociliary Function in Cystic Fibrosis Airways. Am J Respir Crit Care Med; 94 (6): 701-710.

The invention claimed is:
1. A compound which has the structural formula:

[H]-[B]-[A];

wherein [H] is a hydrophilic group, [B] is a subsite recognition group and [A] is a binding group;
wherein [A] has the formula:

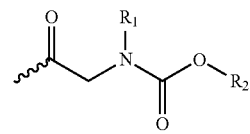

wherein $R_1$ is optionally substituted alkyl, optionally substituted heteroalkyl, optionally substituted aryl, or optionally substituted heteroaryl, and
$R_2$ is cycloalkyl, heterocycloalkyl, aryl, or heteroaryl, wherein said cycloalkyl, heterocycloalkyl, aryl or heteroaryl is optionally substituted; and
wherein [B] has the structure:
(i) -[CO—$CH_2$—$NR^3$]$_m$-,
(ii) -[AA1-AA2]-,
(iii) -(AA1-CO—$CH_2NR^3$)-,
(iv) —(CO—$CH_2$—$NR^3$-AA1)-, or
(v) —(CO—$CH_2$—$NR^4$-AA1-AA3)-;
wherein $R^3$ is H or alkyl; m is 1-2; $R^4$ is H, alkyl or a basic group; and AA1, AA2 and AA3 are amino acid residues, each of which, when linked to another of AA1, AA2 and AA3 are linked through a reverse amide bond.
2. The compound according to claim 1, wherein $R_1$ is selected from the group consisting of $CH(CH_3)_2$, benzyl, n-guanidino propyl, and n-amino butyl.
3. The compound according to claim 1, wherein the compound is selected from the group consisting of Biotin-PEG-NH-Gly-Gly-N-(iso-propyl)-glycine succinimidyl carbamate, Biotin-PEG-NH-Gly-Gly-N-(benzyl)-glycine succinimidyl carbamate, Biotin-PEG-NH-Gly-Gly-N-(n-guanidino-propyl)-glycine succinimidyl carbamate, Biotin-PEG-NH-Gly-Gly-N-(n-amino-butyl)-glycine succinimidyl carbamate, Biotin-PEG-NH—N-(n-guanidino-propyl)-glycine-Gln-Sar-N-(n-guanidino-propyl)-glycine succinimidyl carbamate, HO-Lys(Biotin)-Ahx-Gly-Gly-N-(n-guanidino-propyl)-glycine succinimidyl carbamate, HO-Lys(Biotin)-Ahx-Gly-Gly-N-(n-guanidino-propyl)-glycine pentafluorophenyl carbamate, Biotin-PEG-NH—N-(n-guanidino-propyl)-glycine N(Val)-N(Lys)N-(n-guanidino-propyl)-glycine succinimidyl carbamate, N-ε-(1-acetylene-3-amino-phenyl)-di-carboxy-pentane-Lys-NH-Ahx-NH-Gly-Gly-N-(n-guanidino-propyl)-glycine succinimidyl carbamate, Biotinyl-(PEG)2-N(Arg)-Asn-N-(n-amino-butyl)-glycine succinimidyl carbamate, and Biotin-PEG-NArg-D-Gln-Sar-NArg-COOSu.
4. A pharmaceutical composition comprising a compound according to claim 1.

5. A compound which has the structural formula:

[H]-[B]-[A];

wherein [H] is a hydrophilic group, [B] is a subsite recognition group and [A] is a binding group;
wherein [A] has the formula:

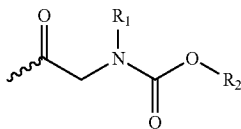

wherein $R_1$ is H, optionally substituted alkyl, optionally substituted heteroalkyl, optionally substituted aryl, or optionally substituted heteroaryl, and wherein $R_2$ is an optionally substituted heteroaryl group or a pentahalo substituted phenyl group; and wherein [B] has the structure:
(i) -[CO—CH$_2$—NR$^3$]$_m$-,
(ii) -[AA1-AA2]-,
(iii) -(AA1-CO—CH$_2$NR$^3$)—,
(iv) —(CO—CH$_2$—NR$^3$-AA1)-, or
(v) —(CO—CH$_2$—NR$^4$-AA1-AA3)-;

wherein $R^3$ is- or alkyl, r is 1-2; $R^4$ is H, alky) or a basic group; and AA1, AA2 and AA3 are amino acid residues each of which, when linked to another of AA1, AA2 and AA3 are linked through a reverse amide bond.

6. A compound which has the structural formula:

[H]-[B]-[A];

wherein [H] is a hydrophilic group, [B] is a subsite recognition group and [A] is a binding group;
wherein [A] has the formula:

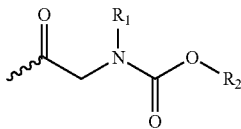

wherein $R_1$ is H, optionally substituted alkyl, optionally substituted heteroalkyl, optionally substituted aryl, or optionally substituted heteroaryl, and $R_2$ is cycloalkyl, heterocycloalkyl aryl, or heteroaryl, wherein said cycloalkyl, heterocycloalkyl, aryl or heteroaryl is optionally substituted; and wherein [B] as the structure:
(i) -[CO—CH$_2$—NR$^3$]$_m$,
(ii) -[AA1-AA2]-,
(iii) -(AA1-CO—CH$_2$NR$^3$)-,
(iv) —(CO—CH$_2$—NR$^3$-AA1)-, or
(v) —(CO—CH$_2$—NR$^4$-AA1-AA3)-;

wherein $R^3$ is H or alkyl; m is 1-2, $R^4$ is H, alkyl or a basic group; and AA1, AA2 and AA3 are amino acid residues each of which, when linked to another of AA1, AA2 and AA3 are linked through a reverse amide bond, and wherein the binding moiety [A] comprises an N-alkyl glycine carbamate moiety.

7. A compound which has the structural formula:

[H]-[B]-[A];

wherein [H] is a hydrophilic group, [B] is a subsite recognition group and [A] is a binding group;
wherein [A] has the formula:

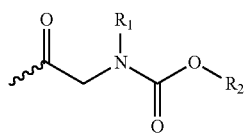

wherein $R_1$ is H, optionally substituted alkyl, optionally substituted heteroalkyl, optionally substituted aryl, or optionally substituted heteroaryl, and $R_2$ is cycloalkyl, heterocycloalkyl, aryl, or heteroaryl, wherein said cycloalkyl, heterocycloalkyl, aryl or heteroaryl is optionally substituted; and wherein [B] has the structure: -[AA1-AA2]-, wherein AA1 is joined to AA2 through a reverse amide bond and AA1 is an amino acid selected from Lys, Arg, Ser, Thr, and Gln, and AA2 is an amino acid selected from Lys and Arg.

8. A compound which has the structural formula:

[H]-[B]-[B]

wherein H is a hydrophilic group, [B] is a subsite recognition group and [A] is a binding group;
wherein [A] has the formula:

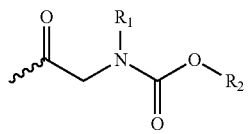

wherein $R_1$ is H, optionally substituted alkyl, optionally substituted heteroalkyl, optionally substituted aryl, optionally substituted heteroaryl, and $R_2$ is cycloalkyl, heterocycloalkyl, aryl, or heteroaryl, wherein said cycloalkyl, heterocycloalkyl, aryl or heteroaryl is optionally substituted; and wherein [B] has the structure:
(i) -[CO—CH$_2$—NR$^3$]$_m$—,
(ii) -[AA1-AA2]-,
(iii) -(AA1-CO—CH$_2$NR$^3$)—,
(iv) —(CO—CH$_2$—NR$^3$-AA1), or
(v) —(CO—CH$_2$—NR$^4$-AA1-AA3)-;

wherein $R^3$ is H or alkyl; m is 1-2; $R^4$ is H, alkyl or a basic group, and AA1, AA2 and AA3 are amino acid residues, each of which, when linked to another of AA1, AA2 and AA3 are linked through a reverse amide bond, and wherein the hydrophilic group comprises a biotin, glucoronyl, or morpholino carbamate group or comprises a moiety having the formula: —NH—(CH$_2$)—(CH$_2$—CH$_2$—O)$_p$—(CH$_2$)$_q$—NH or NH—(CH$_2$)$_o$—(CH$_2$—CH$_2$—O)$_p$—(CH$_2$)$_q$—CO—NH—(CH$_2$)$_q$—NH;

wherein o is 0, 1, 2 or 3; p is 1-10, q is 1, 2 or 3, and r is 1, 2 or 3.

* * * * *

UNITED STATES PATENT AND TRADEMARK OFFICE
CERTIFICATE OF CORRECTION

PATENT NO. : 11,104,703 B2
APPLICATION NO. : 16/344122
DATED : August 31, 2021
INVENTOR(S) : Walker et al.

Page 1 of 1

It is certified that error appears in the above-identified patent and that said Letters Patent is hereby corrected as shown below:

In the Claims

Claim 5 at Column 35, Line 26 should read as follows:
"wherein R3 is H or alkyl, m is 1-2; R4 is H, alkyl or a basic"

Claim 6 at Column 35, Line 51 should read as follows:
"wherein [B] has the structure:"

Claim 8 at Column 36, Line 26 should read as follows:
"[H]-[B]-[A]"

Claim 8 at Column 36, Line 57 should read as follows:
"a moiety having the formula: -NH-(CH2)o-(CH2-"

Claim 8 at Column 36, Line 59 should read as follows:
"CH2-O)p-(CH2)q-CO-NH-(CH2)r-NH;"

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*